(12) United States Patent
Koch

(10) Patent No.: US 9,029,537 B2
(45) Date of Patent: *May 12, 2015

(54) ELECTROLUMINESCENT MATERIALS

(71) Applicant: Lomox Limited, Wilmslow, Cheshire (GB)

(72) Inventor: Gene Carl Koch, North Wales (GB)

(73) Assignee: Lomox Limited, Wilmslow, Cheshire (GB)

( * ) Notice: Subject to any disclaimer, the term of this patent is extended or adjusted under 35 U.S.C. 154(b) by 0 days.

This patent is subject to a terminal disclaimer.

(21) Appl. No.: 13/949,719

(22) Filed: Jul. 24, 2013

(65) Prior Publication Data

US 2013/0317233 A1 Nov. 28, 2013

Related U.S. Application Data

(63) Continuation of application No. 12/811,968, filed as application No. PCT/GB2009/000012 on Jan. 7, 2009, now Pat. No. 8,558,013.

(30) Foreign Application Priority Data

Jan. 7, 2008 (GB) .................................. 0800192.7

(51) Int. Cl.
- C07D 239/26 (2006.01)
- H01L 51/00 (2006.01)
- C07D 249/08 (2006.01)
- C07D 519/00 (2006.01)
- C09K 11/06 (2006.01)
- H01L 51/50 (2006.01)

(52) U.S. Cl.
CPC .......... *H01L 51/0058* (2013.01); *C07D 249/08* (2013.01); *C07D 519/00* (2013.01); *C09K 11/06* (2013.01); *C09K 2211/1416* (2013.01); *C09K 2211/1425* (2013.01); *C09K 2211/1433* (2013.01); *C09K 2211/1466* (2013.01); *H01L 51/0036* (2013.01); *H01L 51/0039* (2013.01); *H01L 51/004* (2013.01); *H01L 51/5012* (2013.01); *Y02E 10/549* (2013.01); *H01L 51/0067* (2013.01); *H01L 51/0074* (2013.01)

(58) Field of Classification Search
CPC .................................................. H01L 51/0058
USPC ...................................... 548/266.2; 544/294
See application file for complete search history.

(56) References Cited

U.S. PATENT DOCUMENTS

| | | | |
|---|---|---|---|
| 4,147,552 A | 4/1979 | Specht et al. | |
| 4,983,324 A | 1/1991 | Durr et al. | |
| 5,834,100 A | 11/1998 | Marks et al. | |
| 6,156,232 A | 12/2000 | Shashidhar et al. | |
| 6,967,437 B1 | 11/2005 | Samuel et al. | |
| 7,075,229 B2 | 7/2006 | Lambertini et al. | |
| 7,118,787 B2 | 10/2006 | O'Neill et al. | |
| 8,263,735 B2 | 9/2012 | Kitano et al. | |
| 8,558,013 B2 | 10/2013 | Koch | |
| 2003/0021913 A1 | 1/2003 | O'Neill et al. | |
| 2003/0099785 A1 | 5/2003 | O'Neill et al. | |
| 2003/0104145 A1 | 6/2003 | Ogawa et al. | |
| 2005/0040396 A1 | 2/2005 | O'Neill et al. | |
| 2005/0082525 A1 | 4/2005 | Heeney et al. | |
| 2005/0116199 A1 | 6/2005 | Kelly et al. | |
| 2005/0146263 A1 | 7/2005 | Kelly et al. | |
| 2005/0147846 A1 | 7/2005 | Marks et al. | |
| 2006/0046092 A1 | 3/2006 | Towns et al. | |
| 2007/0096078 A1 | 5/2007 | Lee et al. | |
| 2007/0134511 A1 | 6/2007 | Kawamura et al. | |
| 2007/0195576 A1 | 8/2007 | Imada et al. | |
| 2007/0254208 A1 | 11/2007 | Kurt et al. | |
| 2007/0264748 A1 | 11/2007 | Sirringhaus et al. | |
| 2008/0248220 A1 | 10/2008 | Sekine et al. | |
| 2011/0015404 A1 | 1/2011 | Koch | |
| 2011/0020566 A1 | 1/2011 | Koch | |
| 2011/0175069 A1 | 7/2011 | Son et al. | |
| 2012/0271052 A1 | 10/2012 | Koch | |
| 2013/0037752 A1 | 2/2013 | Koch | |
| 2013/0163928 A1 | 6/2013 | Wang et al. | |
| 2013/0228759 A1 | 9/2013 | Koch et al. | |

FOREIGN PATENT DOCUMENTS

| | | |
|---|---|---|
| CN | 1711301 | 12/2005 |
| CN | 101085916 | 12/2007 |
| CN | 101333162 | 12/2008 |

(Continued)

OTHER PUBLICATIONS

Aldred et al., "Linearly Polarised Organic Light-Emitting-Diodes (OLEDs): Synthesis and Characterisation of a Novel Hole-Transporting Photoalignment Copolymer", Journal of Material Chemistry, Jun. 2005, vol. 15, pp. 3208-3213.

Aldred et al., "A Full-Color Electroluminescent Device and Patterned Photoalignment Using Light-Emitting Liquid Crystals", Advanced Materials, Jun. 2005, vol. 17, No. 11, pp. 1368-1372.

Contoret et al., "The Photopolymerization and Cross-Linking of Electroluminescent Liquid Crystals Containing Methacrylate and Diene Photopolymerizable End Groups for Multilayer Organic Light-Emitting Diodes", Chemistry Materials, Apr. 2002, vol. 14, No. 4, pp. 1477-1487.

(Continued)

*Primary Examiner* — Taofiq A Solola
(74) *Attorney, Agent, or Firm* — Dority & Manning, P.A.

(57) ABSTRACT

Compounds of the general structure: $Z-A-(S-B)_n$ where A represents a linear aromatic molecular core, S represents a flexible spacer unit, B represents a crosslinking group such as a methacrylate group, n equals 1 to 3, and Z represents any entity compatible with the B groups, and in which A is a substantially aromatic nucleus containing fluorene ring structures substituted at the 9-position and in which the 9-positions of the fluorenes are not susceptible to oxidation.

18 Claims, 1 Drawing Sheet

(56) References Cited

FOREIGN PATENT DOCUMENTS

| | | |
|---|---|---|
| EP | 1215192 | 6/2002 |
| EP | 1385041 | 1/2004 |
| EP | 1 394 188 | 3/2004 |
| EP | 1 598 387 | 11/2005 |
| EP | 2194582 | 9/2008 |
| GB | 2456298 | 7/2009 |
| JP | H03-013952 | 1/1991 |
| JP | 2001-166519 | 6/2001 |
| JP | 2002-040686 | 2/2002 |
| JP | 2003-043713 | 2/2003 |
| JP | 2004-212959 | 7/2004 |
| JP | 2005-036223 | 2/2005 |
| JP | 2005-206750 | 8/2005 |
| JP | 2009-124064 | 6/2009 |
| WO | WO 9749548 | 12/1997 |
| WO | WO 00-70691 | 11/2000 |
| WO | WO 2004-041901 | 5/2004 |
| WO | WO 2004-093154 | 10/2004 |
| WO | WO 2005-001952 | 1/2005 |
| WO | WO 2005-034184 | 4/2005 |
| WO | WO 2005/057675 | 6/2005 |
| WO | WO 2005-095543 | 10/2005 |
| WO | WO 2005-121150 | 12/2005 |
| WO | WO 2006-058182 | 6/2006 |
| WO | WO 2006-058266 | 6/2006 |
| WO | WO 2006-058267 | 6/2006 |
| WO | WO 2006-060294 | 6/2006 |
| WO | WO 2006-131185 | 12/2006 |
| WO | WO 2007/064721 | 6/2007 |
| WO | WO 2009/087364 | 7/2009 |
| WO | WO 2009/103952 | 8/2009 |
| WO | WO 2010/061896 | 6/2010 |
| WO | WO 2011/039506 | 4/2011 |

OTHER PUBLICATIONS

Decker et al., "Photoinitiated Radical Polymerization of Vinyl Ether-Maleate Systems", Polymer, vol. 38, No. 9, 1997, pp. 2229-2237.
Kohli et al., "Co-Polymerization of Maleimides and Vinyl Ethers: A Structural Study", Macromolecules, vol. 31, No. 17, 1998, pp. 5681-5689.
Lee et al., "Novel Photo-Alignment Polymer Layer Capable of Charge Transport", Macromolecular Chemistry and Physics, Nov. 2004, vol. 205, Issue 16, pp. 2245-2251.
Loy et al., "Thermally Stable Hole-Transporting Materials Based Upon a Fluorene Core", Advanced Functional Materials, Apr. 2002, vol. 12, No. 4, pp. 245-249.
Neilson et al., "Synthesis and Properties of Perfluorocyclobutyl (PFCB) Polymers for Light Emission", Polymer Preprints, 2005, vol. 46, No. 2, pp. 653-654.
Yak et al., "Synthesis and Characterization of Spiro-Triphenylamine Configured Polyfluorene Derivatives with Improved Hole Injection", Macromolecules, vol. 39, No. 19, 2006, pp. 6433-6439.
Yu et al., "Fluorene-Based Light-Emitting Polymers", Chinese Journal of Polymer Science, Dec. 2001, vol. 19, No. 6, pp. 603-613.
IPRP for PCT/GB2009/000012, Issued Jul. 13, 2010.
IPRP for PCT/GB2009/000415, Issued Aug. 24, 2010.
IPRP for PCT/EP2011/065971, Completed Jan. 26, 2012.
Search Report for PCT/GB2013/000201, Mailed May 8, 2013.
IPRP for PCT/GB2010/001818, Issued Apr. 3, 2012.
IPRP for PCT/GB2010/001817, Issued Apr. 3, 2012.
Hay-Lei Cui et al., "Dual Organocatalysis: Asymmetric Allylic-Allylic Alkylation of [alpha], [alpha]-Dicyanoalkenes and Morita-Baylis-Hillman Carbonates," Chemistry—A European Journal, vol. 15, No. 7, Feb. 2, 2009, pp. 1574-1577.
Alvaro et al., "Stereoselective synthesis of substituted 2,5-diazabicyclo[2.2.1]heptanes by iodine-mediate cyclization of optically pure compounds containing the 4,5-diamino-1,7-octadiene and 1,2-diamino-4-alkene moieties", Tetrahedron, vol. 63, No. 50, Oct. 31, 2007, pp. 12446-12453.
Bassindale, M. J. et al., "Employment of a cyclobutene ring-opening metathesis reaction towards a concise synthesis of (+/−)-sporochnol A," Tetrahedron Letters, vol. 42, No. 51, Dec. 17, 2001, pp. 9055-9057.
Goel et al., "Donor-Acceptor 9-Uncapped FLuorenes and Fluorenones as Stable Blue Light Emitters," Org. Letters 2009, vol. 11, pp. 1289-1292.
Perepichka et al., "Thiophene-Based materials for Electroluminescent Applications," Handbook of Thiophene-Based Materials: Applications in Organic Electronics and Photonics 2009, Chapter 19, pp. 695-756.

ELECTROLUMINESCENT MATERIALS

CROSS-REFERENCE TO RELATED APPLICATIONS

The present application is a continuation of U.S. application Ser. No. 12/811,968 having a filing date of Jul. 7, 2010; which is a National Stage Entry of PCT/GB09/00012 having a filing date of Jul. 1, 2009; based on GB 0800192.7 having a filing date of Jan. 7, 2008. Applicant claims priority to and benefit of all such applications and incorporate all such applications herein by reference.

BRIEF DESCRIPTION OF THE DRAWINGS

A full and enabling disclosure of the present invention, including the best mode thereof to one skilled in the art, is set forth more particularly in the remainder of the specification, which includes reference to the accompanying figures, in which.

DETAILED DESCRIPTION

Figure 1:
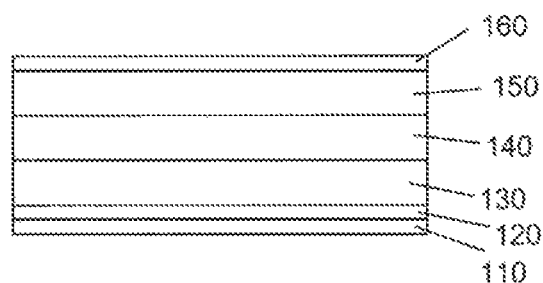
FIG. 1 illustrates a prior art OLED configuration.

This invention relates to electroluminescent materials.

It is known that some reactive mesogens (liquid crystalline materials capable of being chemically crosslinked into a polymer matrix) of the general formula:

B-S-A-S-B where A represents a linear aromatic molecular core, S represents flexible spacer units and B represents crosslinking groups such as methacrylate groups, may be useful in the fabrication of organic electronic devices. This is particularly the case if B represents photocrosslinkable groups, since then the materials function essentially as photoresists, which is to say, thin layers of these materials may be patterned into useful electronic structures by patterned exposure to light, particularly UV light.

Further, if the a linear aromatic core A is luminescent in nature, these reactive mesogens materials may be patterned into the active light emitting layers in electroluminescent devices such as organic light emitting diodes (OLEDS) and organic diode lasers.

One example of such a material is represented by the structure:

Here, the core aromatic structure A is a fluorine ring system:

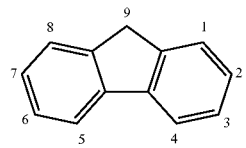

substituted at the 2 and 7 ring positions with aromatic (phenylthienyl) groups and at the two 9 positions with alkyl groups (in this case, n-propyl groups). The B groups are penta-1,4-diene-3-yl groups useful for crosslinking the materials.

All working OLED devices produced to date of materials of the general structure

B-S-A-S-B in which A contained 9,9-dialkylfluorene structures have had disappointingly low lifetimes.

The present invention provides materials of that general structure, and of other structures involving the -A-S-B subunit that have commercially useful lifetimes.

The invention comprises compounds of the general structure:

Z-A-(S-B)$_n$ where A represents a linear aromatic molecular core, S represent a flexible spacer unit, B represents a crosslinking group such as a methacrylate group, n equals 1 to 3, and Z represents any entity compatible with the B groups, and in which A is a substantially aromatic nucleus containing fluorene ring structures substituted at the 9-position and in which the 9-positions of the fluorenes are not susceptible to oxidation.

By 'compatible with the B groups' is meant that the Z entity will join to the B groups or at least will not interfere with B groups of different molecules joining to each other.

In one class of compounds, the Z will comprise S-B-, and n=1, so that the compound has the general structure B-S-A-S-B.

S may represent a flexible spacer comprising a chain of single bonded atoms. The chain may comprise an alkyl chain. The alkyl chain may contain one or more hetero atoms.

B may represent a crosslinking chemical group, which may be a methacrylate group or a 1,4-pentadien-3-yl group.

A may represent a substantially linear, covalently bonded chain, which may be a chain of aromatic or heteroaromatic diradicals represented by the general formula:

Structure I

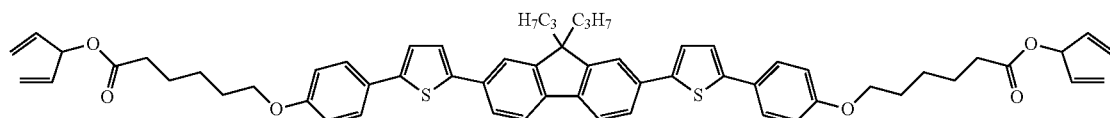

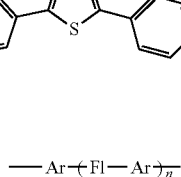

Ar may be an aromatic or heteroaromatic diradical, and may comprise a 1,4-phenylene, a biphenyl-4,4'-diyl, a terphen-4,4"-diyl, a naphthalene-1,4-diyl, a thiophene-2,5-diyl, a pyrimidine-2,5-diyl, a perylene-3,10-diyl, a pyrene-2,7-diyl, a 2,2'-dithiophen-5,5'-diyl, a an oxazole-2,5-diyl, a thieno[3,2-b]thiophene-2,5-diyl, a dithieno[3,2-b:2',3'-d]thiophene-2,6-diyl, or a imidazo[4,5-d]imidazole-2,5-diyl diradical, or a single bond.

Fl may be:

Structure 2

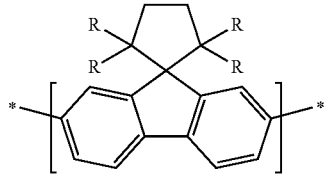

(spiro[cyclopentane-1,9'-fluorene]-2',7'-diyl diradicals)

or

Structure 3

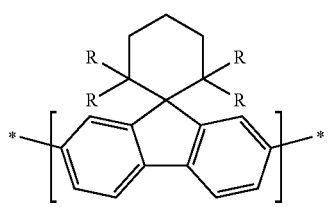

(spiro[cyclohexane-1,9'-fluorene]-2',7'-diyl diradicals)

or

Structure 4

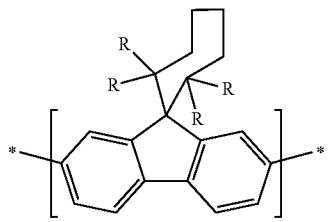

(spiro[cycloheptane-1,9'-fluorene]-2',7'-diyl diradicals)

or

Structure 5

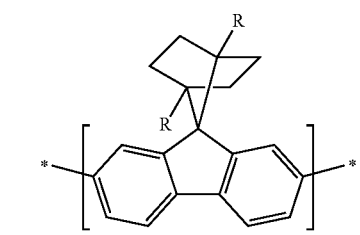

(spiro[bicyclo[2,2,1]heptane-7,9'-fluorene]-2',7'-diyl diradicals)

or

Structure 6

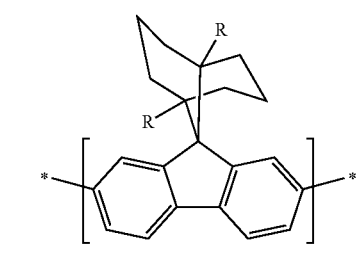

(spiro[bicyclo[3,3,1]nonane-9,9'-fluorene]-2',7'-diyl diradicals)

Structure 7

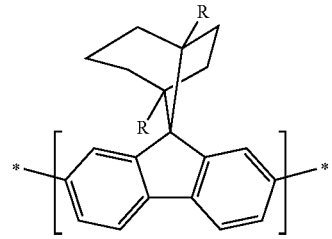

(spiro[bicyclo[3,2,1]octane-8,9'-fluorene]-2',7'-diyl diradicals)

or

Structure 8

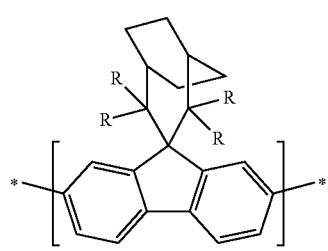

(spiro[bicyclo[3,2,2]nonane-3,9'-fluorene]-2',7'-diyl diradicals)

or

Structure 9

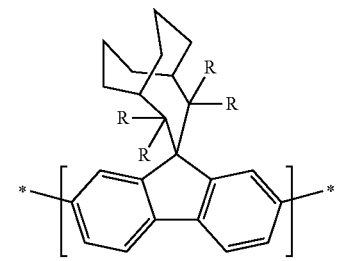

(spiro[bicyclo[3,3,3]undecane-3,9'-fluorene]-2',7'-diyl diradicals)

or

Structure 10

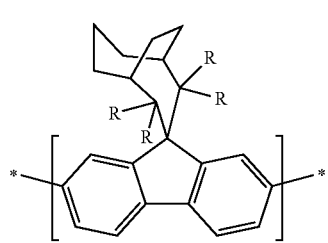

(spiro[bicyclo[3,3,2]decane-3,9'-fluorene]-2',7'-diyl diradicals)

or

Structure 11

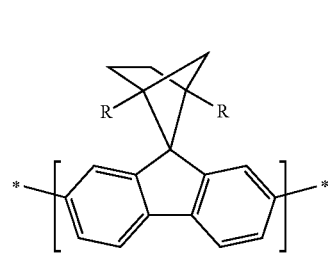

(spiro[bicyclo[2,1,1]hexane-5,9'-fluorene]-2',7'-diyl diradicals)

or

Structure 12

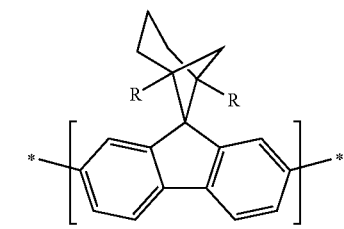

(spiro[bicyclo[3,1,1]heptane-6,9′-fluorene]-2′,7′-diyl diradicals)

Structure 13

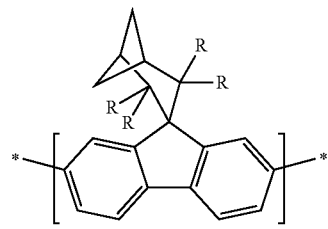

(spiro[bicyclo[3,1,1]heptane-3,9′-fluorene]-2′,7′-diyl diradicals)

Structure 14

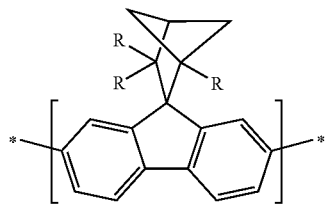

(spiro[bicyclo[2,1,1]hexane-2,9′-fluorene]-2′,7′-diyl diradicals)

Structure 15

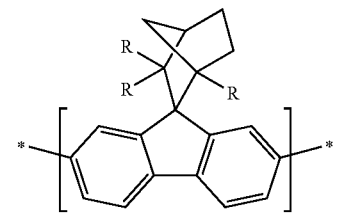

(spiro[bicyclo[2,2,1]heptane-2,9′-fluorene]-2′,7′-diyl diradicals)

Structure 16

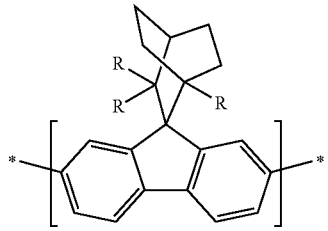

(spiro[bicyclo[2,2,2]octane-2,9′-fluorene]-2′,7′-diyl diradicals)

Structure 17

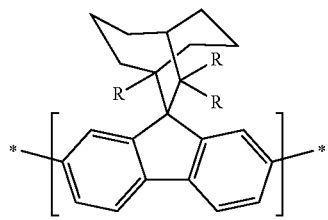

(spiro[bicyclo[3,3,2]decane-9,9′-fluorene]-2′,7′-diyl diradicals)

Structure 18

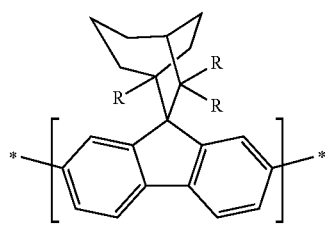

(spiro[bicyclo[3,2,2]nonane-6,9′-fluorene]-2′,7′-diyl diradicals)

Structure 19

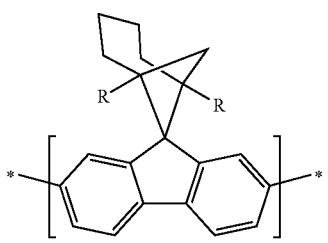

(spiro[bicyclo[4,1,1]octane-7,9′-fluorene]-2′,7′-diyl diradicals)

Structure 20

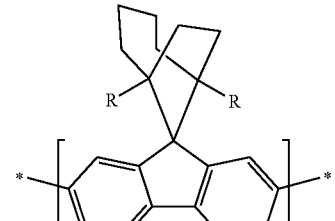

(spiro[bicyclo[4,2,1]nonane-9,9′-fluorene]-2′,7′-diyl diradicals)

Structure 21

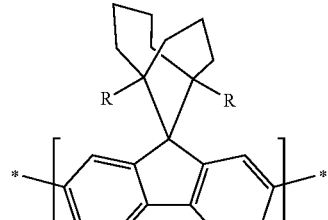

(spiro[bicyclo[4,3,1]decane-10,9′-fluorene]-2′,7′-diyl diradicals)

Structure 22

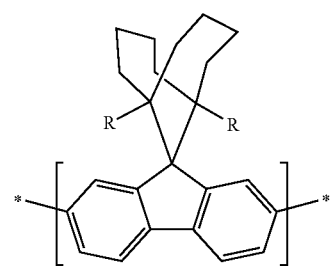

(spiro[bicyclo[4,4,1]undecane-11,9'-fluorene]-2',7'-diyl diradicals)

R may be hydrogen or an alkyl group containing one to five carbons, and may in particular be a methyl or ethyl group.

It is preferable that the 9-position in these tetra-alkyl substituted materials has steric shielding from attack by reactive species. Preferably, all the R groups are alkyls, and, more preferably, all the same.

Preferably, the n subscript in the formula for A is from 3 to 6.

The invention also comprises a light emitting or charge transporting material of the general structure:

S-A-S, wherein A is a substantially rigid, rod-shaped molecular core comprising a chain of aromatic or heteroaromatic diradicals represented by the general formula:

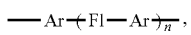

wherein Fl comprises a fluorene-2,7-diyl diradical spiro substituted at the 9 position on the fluorene ring with an alicyclic ring system, wherein the alicyclic substituent has no hydrogen substituted on the two carbon atoms immediately adjacent the carbon atom at position 9 in the fluorene ring system, wherein Ar is chosen independently from aromatic or heteroaromatic diradicals or single bonds, and wherein S are flexible spacer units.

The material may be liquid crystalline.

'n' may be between 1 and 10.

The material may be a polymer.

The invention also comprises a light emitting or charge transporting polymer of the general structure:

T-A-T, wherein A is a substantially linear, covalently bonded chain comprising a chain of aromatic or heteroaromatic diradicals represented by the general formula:

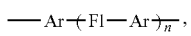

wherein Fl comprises a fluorene-2,7-diyl diradical spiro substituted at the 9 position on the fluorene ring with an alicyclic ring system, wherein the alicyclic substituent has no hydrogen substituted on the two carbon atoms immediately adjacent the carbon atom at position 9 in the fluorene ring system, wherein Ar is chosen independently from aromatic or heteroaromatic diradicals or single bonds, and wherein T are polymer chain terminating units.

T may be independently selected from hydrogen, halogen, aryl, or aryl substituted with a cyano, hydroxyl, glycidyl ether, acrylate ester, methacrylate ester, ethenyl, ethynyl, maleimide, nadimide, trialkylsiloxy, or trifluorovinyl ether moieties.

Three-dimensional models of the materials described above show them to be no more bulky than similar material in which the fluorene 9-positions are substituted with straight chain alkyl groups. Therefore, the nematic phase in these materials should be just as stable as in the previous materials.

The preferred embodiment of the above materials is one in which all of the R groups are alkyls. This is because these materials have no hydrogen substituents a to the fluorene ring system. Hydrogens in these positions are at least partially benzylic in character and are thought to be implicated in oxidation at the nine position. Also, in these preferred completely alkyl-substituted materials the 9-position has the greatest steric shielding from attack by reactive species.

It is also preferable that the spiro[cyclopentane-1,9'-fluorene]-2',7'diyl (Structure 2), spiro[cyclohexane-1,9'-fluorene]-2',7'diyl (Structure 3), spiro[cycloheptane-1,9'-fluorene]-2',7'diyl (Structure 4), spiro[bicyclo[2,2,1]heptane-7,9'-fluorene]-2',7'diyl (Structure 5), or spiro[bicyclo[3,3,1]nonane-9,9'-fluorene]-2',7'diyl (Structure 8) diradicals are chosen as the F units in the general formula of the invention because of their symmetry and ease of synthesis.

Still further, it is preferable that all the R substituents are the same. This is because molecules in which the R substituents are different will show positional or stereoisomerism that will complicate the electronic level purification required for these materials.

The compounds of the invention containing diradicals F with structures 2 through 22 may be further substituted at positions (other than those that are substituted already with R groups) on the cycloaliphatic and bicycloaliphatic rings that are joined to the fluorene ring structures at their 9-positions. However, compounds with substituents at these other positions are less preferred because of the potential for geometrical or stereoisomerism that will complicate their purification. An exception is that compounds with structures Structure 23

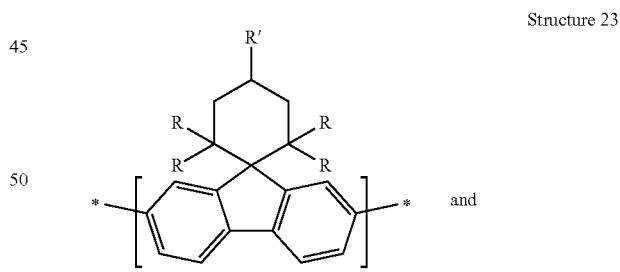

and

Structure 24

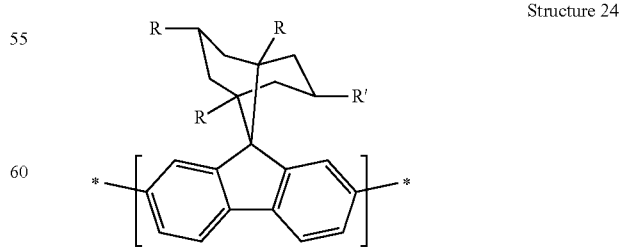

wherein R is as above and R' are preferably selected from alkyls ranging from $CH_3-$ to $C_5H_{11}-$ in chain length, are useful.

An additional aspect of the invention is that nitrogen atoms may be substituted for some or all of the carbon atoms at positions 1, 3, 4, 5, 6, and 8 of the fluorene ring systems of the F diradicals of structures 2-24.

Emitter materials of the invention in which the n subscript in the formula for A is equal to between 3 and 6 are preferred.

Lower n values lead to molecules with lower light emission efficiency. Higher n values lead to molecules that are more difficult to synthesise and/or more difficult to purify.

The following are some exemplary compounds of the invention:

Structure 25

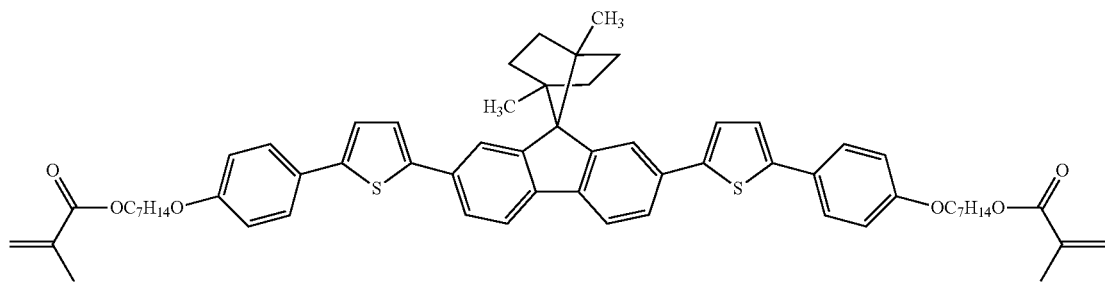

Structure 26

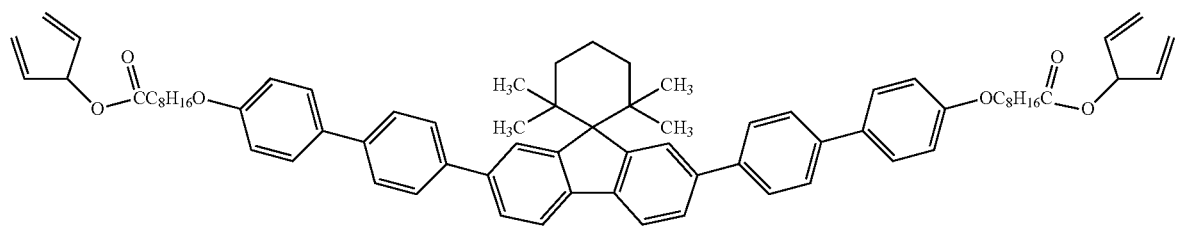

Structure 27

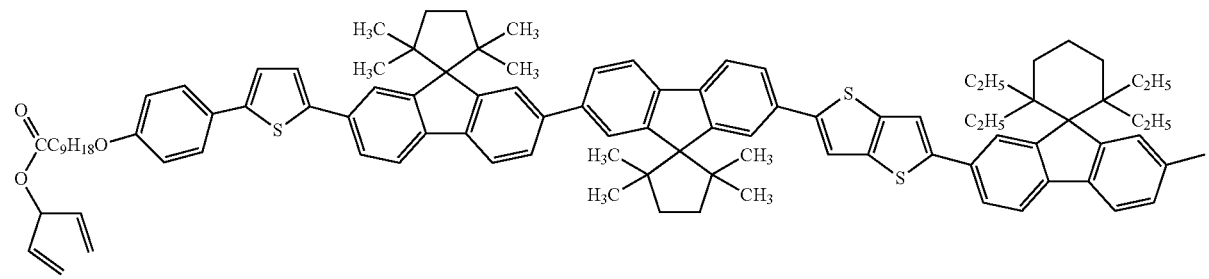

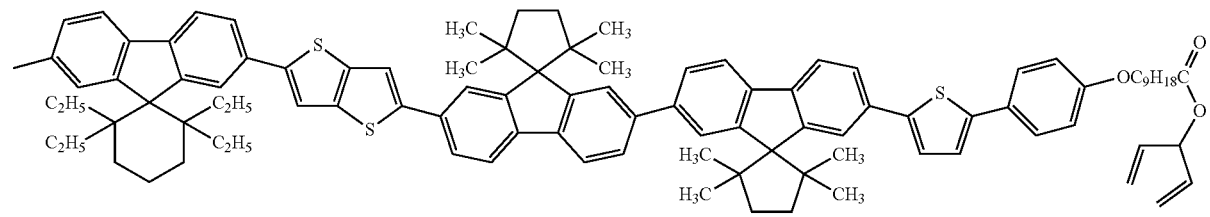

Structure 28

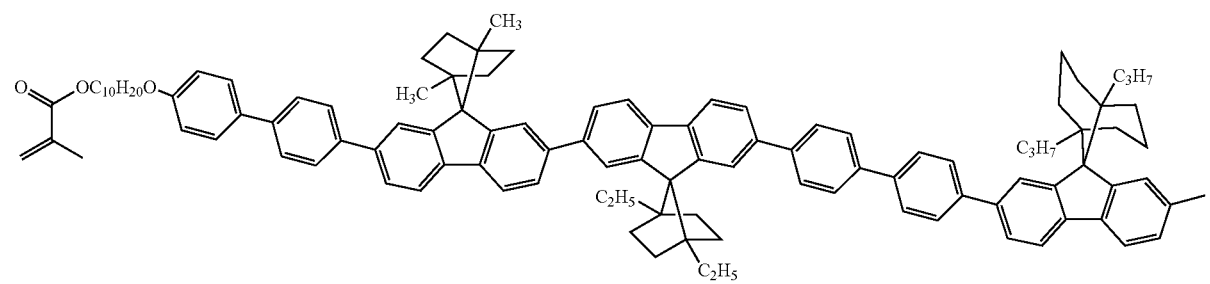

-continued
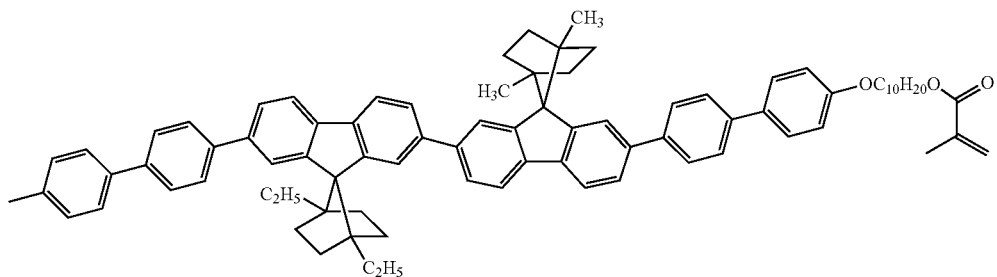
Structure 29
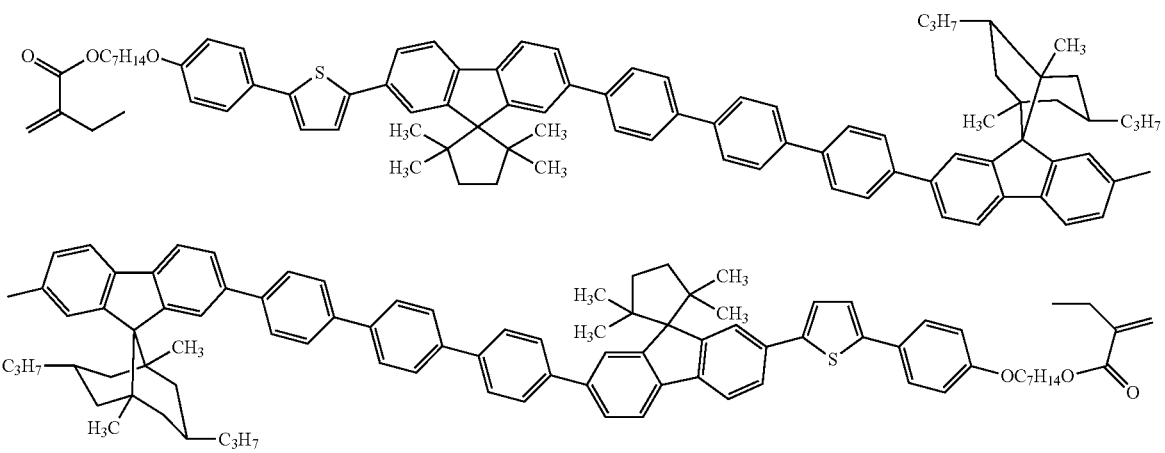
Structure 30
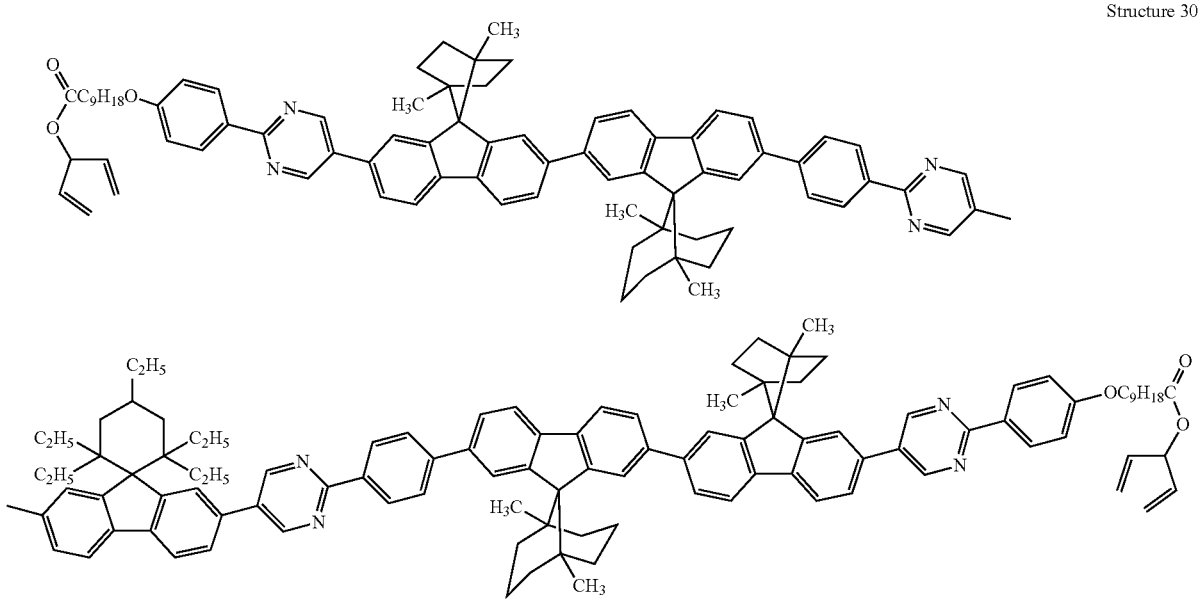
Structure 31
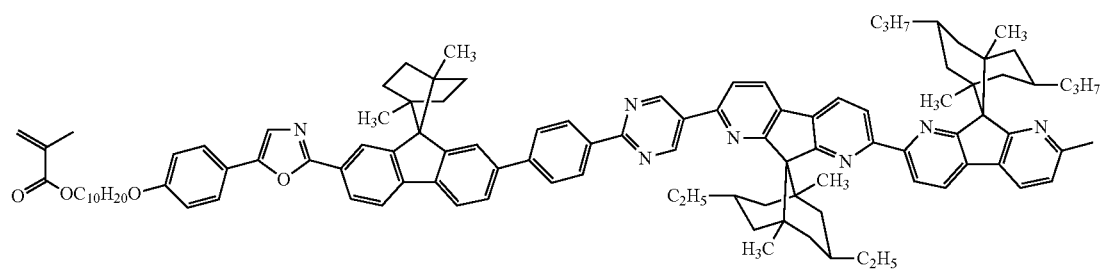

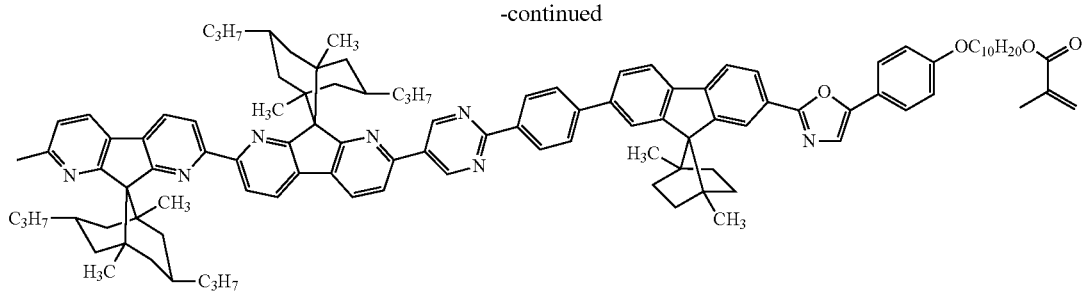
Structure 32
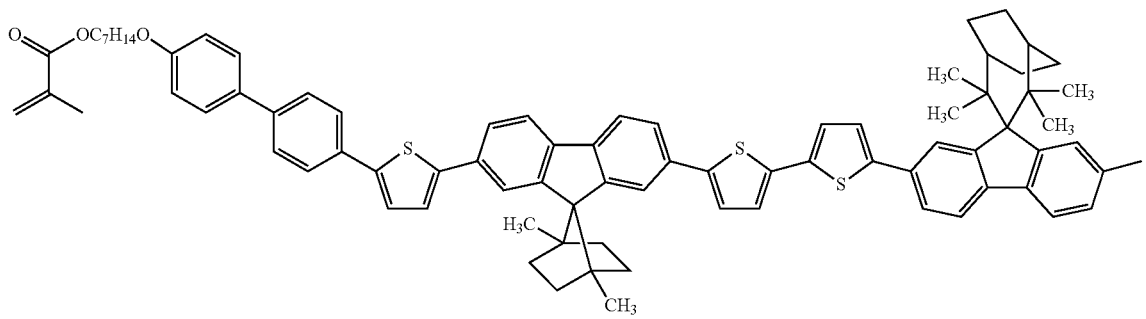
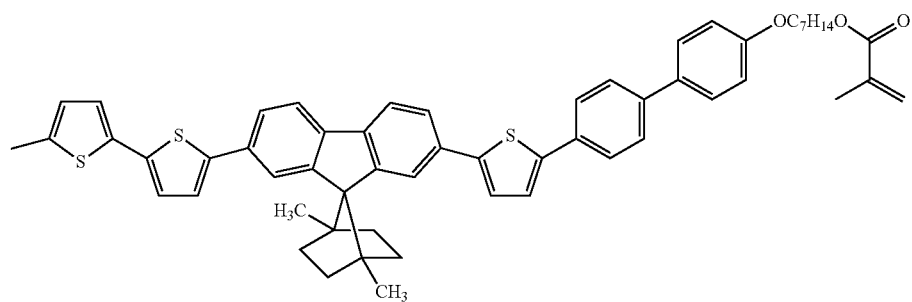
Structure 33
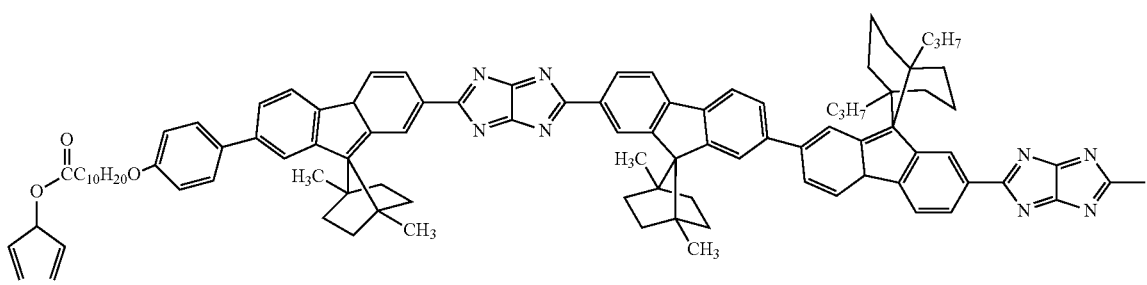
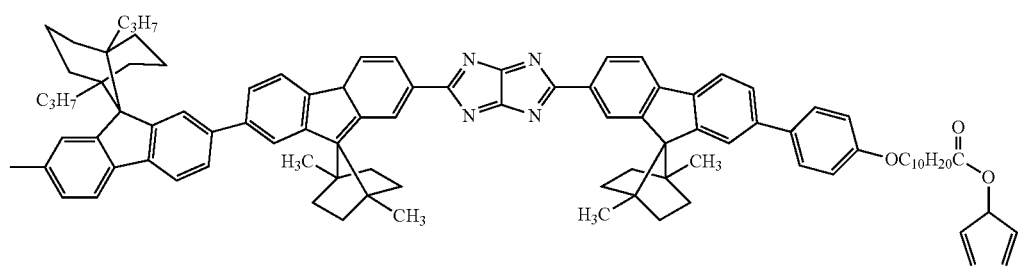

-continued
Structure 34
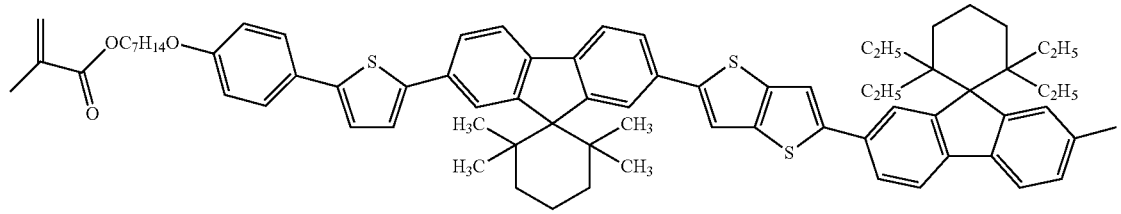
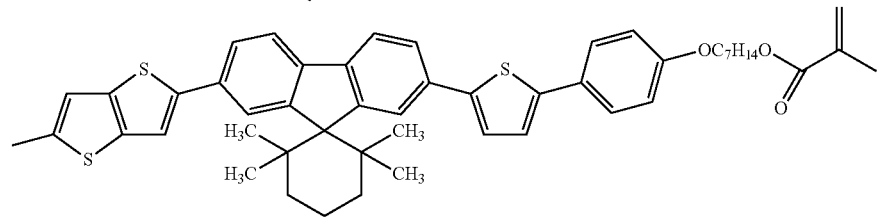
Structure 35
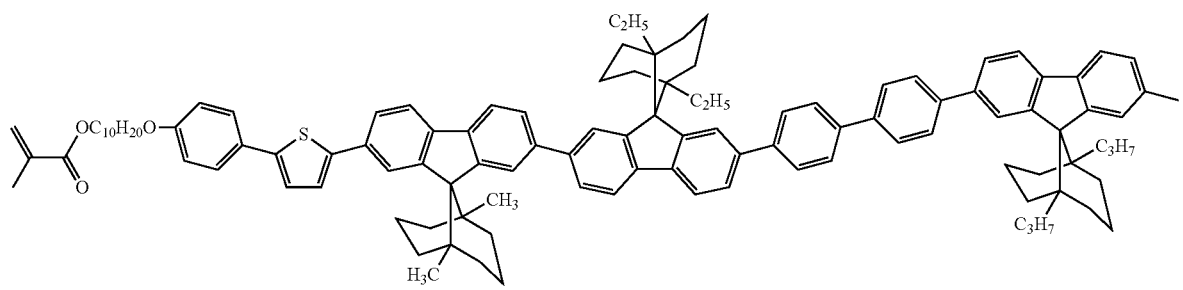
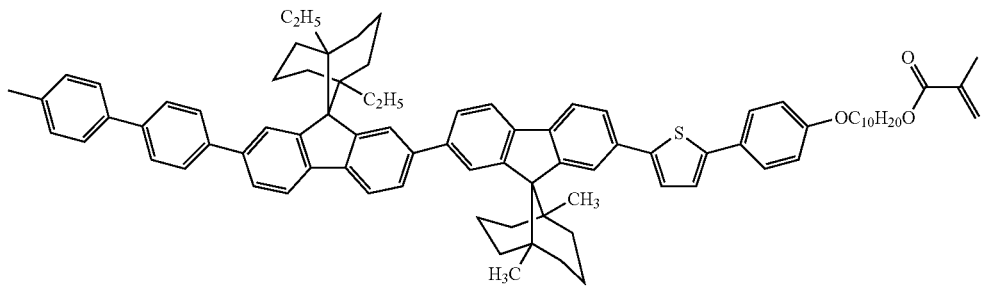
Structure 36
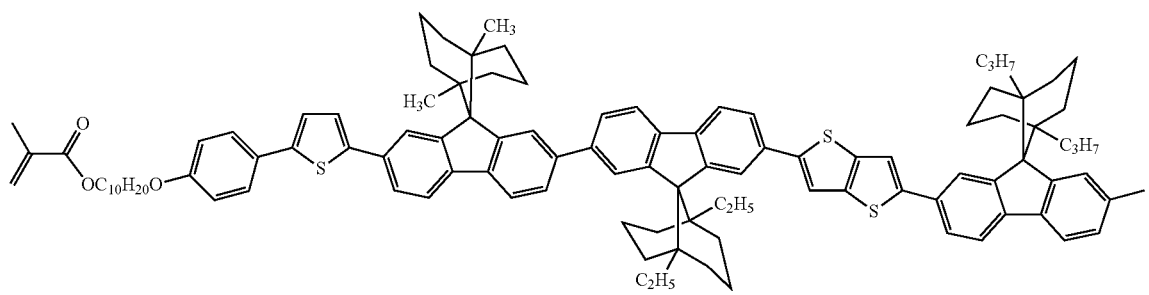
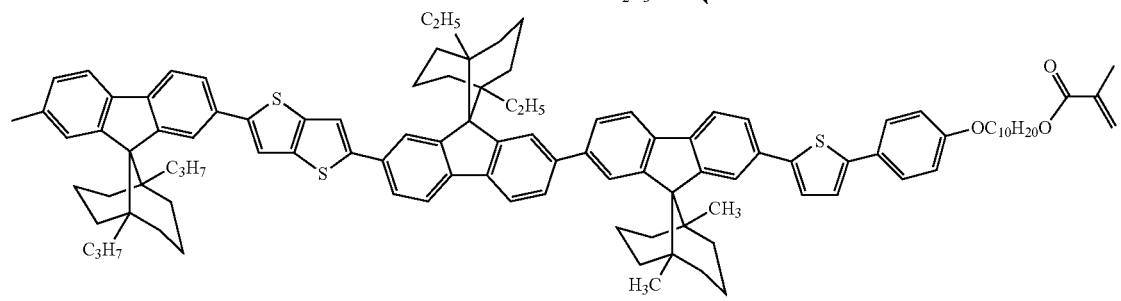

Materials according to this invention may be mixed together to form liquid crystalline mixtures. This can be very advantageous from the standpoint of optimising the properties of the materials. For instance, individual compounds of the invention may have liquid crystal to isotropic liquid transition temperature far below their melting points (monotropic liquid crystalline phases). In device fabrication applications this can lead to glassy or supercooled liquid films of the materials that are sufficiently thermodynamically unstable so as to lead to the danger of crystallisation within the film and subsequent destruction of useful electronic properties. Mixing multiple component compounds together can depress the melting point of the resulting mixtures below the liquid crystal to isotropic liquid transition temperatures or at least sufficiently suppress crystallisation so as to eliminate this problem.

Another advantage of using mixtures of the materials of the invention is that it may allow materials with otherwise highly useful device application properties to be used even though they a have a particular property that renders them unusable as a pure material. For instance it may be desired to prepare a light emitting polymer film having a nematic liquid crystalline structure. A compound of the invention may be a light emitting material of very high efficiency and possess other useful properties, but at the same time may be found to possess a smectic rather than a nematic liquid crystalline phase. By dissolving said desirable compound into a mixture of other compounds of the invention that have nematic phases, a mixture having the light emission properties of the first highly desirable material combined with a nematic phase structure may result.

It is often also desirable to reduce the self-absorption of emitted light by organic luminescent materials. This self-absorption occurs because the spectral absorbance and emission bands of organic luminescent materials overlap to a greater or lesser extent in various materials. A solution to this problem well known, for instance, in the field of dye lasers is to dissolve the luminescent material in a host with that absorbs light at a shorter wavelength than the luminescent solute. If the solution is dilute, for instance one to two percent, the self-absorption of the luminescent solute is nearly completely suppressed. The facile mutual miscibility of the various compounds of this invention makes the preparation of solutions of this type very easy.

In organic light emitting device applications it is necessary that there be facile excitation energy transfer from the host material to the solute luminescent material. This is because charge carriers (electrons and holes) must be transported through the host medium to recombine to form the excitons (electrically excited molecular orbital states) that radiate light. In a mixture composed mainly of component host molecules this recombination and exciton formation will mainly occur in the host molecules. The excitation energy then needs to be transferred from the host molecules into the luminescent solute molecules. It is a requirement for this energy transfer that the spectral luminescent emission band(s) of the host material overlap the absorption band of the luminescent solute. Thus an important aspect of the invention is the preparation of mixtures of the compounds of the invention that have this spectral relationship between the constituent components. For instance, compound 28, which emits in the blue region of the spectrum, can serve as a host for compound 27, which is a green light emitter. A polymer film prepared by the UV induced crosslinking of a solution of 5% compound 27 in compound 28 will exhibit considerably less self-absorption of the green light emitted by 27 than will a film prepared by UV crosslinking of pure 27.

Another aspect of the invention relates to the balanced transport and insertion of positive and negative charge carriers into the electrically active regions or layers of devices. As an example, a typical (prior art) OLED configuration is shown in FIG. 1. This device contains an anode 110 usually prepared as a conductive indium-tin oxide film on a glass substrate, a hole injection layer 120 that supports facile injection of holes into the hole transporting layer 130. The hole-transporting layer 130 in the case of this invention is a polymerised film of a compound or a mixture of compounds of the invention that is chosen for its high mobility for holes. The device further consists of a cathode 160 that injects electrons into electron transporting layer 150. There may be an optional electron injection layer (not shown) between cathode 160 and electron transporting layer 150. Electron transporting layer 150 and hole transporting layer 130 insert respectively electrons and holes into light emitting layer 140 where they recombine to form excitons and then light. The electron-transporting layer 150 of this invention is a polymerised film of a compound or mixture of compounds of the invention that is chosen for its high mobility for electrons. The light-emitting layer of this invention is also a polymerised film of a compound or mixture of compounds of the invention.

A further function of electron transporting layer 150 is to prevent holes injected into 140 from continuing onward out the other side of 140 and eventually recombining with electrons at the surface of the cathode in a non-light emissive event. To effect this the material(s) of 150 are chosen so as to have a HOMO (highest occupied molecular orbital) energy level that is quite low as compared to the HOMO energy level of the light emitting layer 140. Usually around 6.5 electron volts below vacuum as opposed to around 5.25 ev below vacuum for the material of 140. The result is that that there is a very high-energy barrier that prevents holes from entering 150. Electron transporting layer materials of this type are said to be hole blocking. A hole blocking, electron transporting reactive mesogen material of the invention is Structure 37

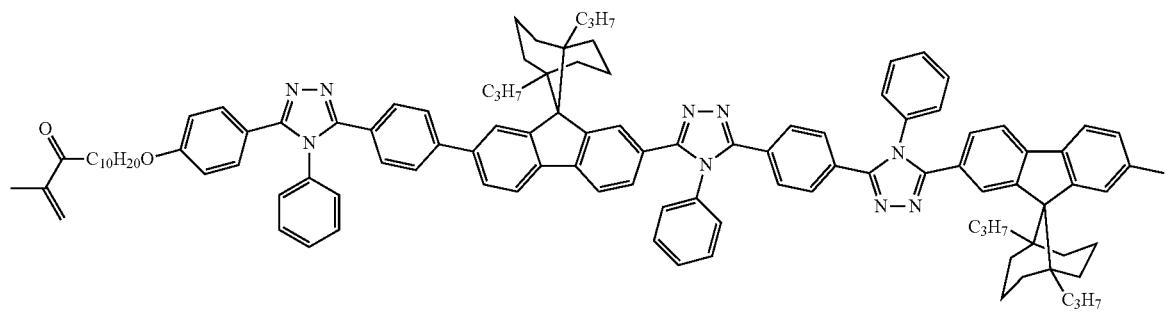

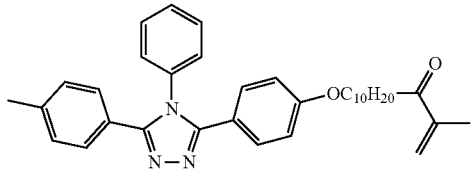

It can be seen that this material is of the type

B-S-A-S-B with A having the structure

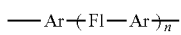

as above, but with Ar now comprising a 3,4,5-triaryl substituted 1,2,4-triazole,

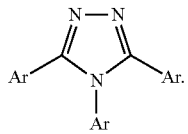

The light-emitting layer 140 of device 100 will perform optimally if electron and hole mobilities in the material are approximately the same. Unfortunately most of the best light emitting materials according to the invention have considerably higher hole mobilities than electron mobilities. However, the ability to produce mixtures of the materials of the invention allows compound 37 and similar compounds to be blended into the light emitting materials of the invention to form mixtures with substantially equal hole and electron mobilities. These mixtures can then be polymerised by UV exposure to form optimised light emitting layers.

Yet another advantage of using mixtures of the materials of the invention is that it allows the use of mixtures of reactive mesogen materials in which photoinitiated electron donor-acceptor interactions as opposed to ionic or free radical initiation are used to initiate polymerization. This may result in much more stable (in terms of shelf-life) reactive mesogen materials than in methacrylate-based systems, while at the same time maintaining low UV crosslinking fluences. In these mixtures at least one of the reactive mesogen materials is substituted with electron-rich crosslinking groups while at least one other component reactive mesogen material is substituted with electron-deficient crosslinking groups. Ultraviolet radiation incident on the material promotes the electron-deficient crosslinking groups on some reactive mesogen molecules into electronically excited states. The excited state, electron-deficient crosslinking groups then abstract electrons from the electron-rich (electron donor) crosslinking groups on other reactive mesogen molecules initiating the copolymerization crosslinking reaction. Descriptions of this mode of photopolymerization may be found in, for example, "Photoinitiated radical polymerization of vinyl ether-maleate systems", *Polymer* 38, (9) pp. 2229-37 (1997); and "Co-Polymerization of Maleimides and Vinyl Ethers: A Structural Study", *Macromolecules* 1998, (31) pp. 5681-89.

Electron-deficient crosslinking groups include maleimides, maleates, fumarates, and other unsaturated esters. Electron donor groups include vinyl ethers, 1-propenyl ethers and other similar alkenyl ethers. Mixtures like these are advantageous in that the individual components are thermally and photochemically stable with excellent shelf-lives. However, when the materials are combined, the mixture has high photochemical sensitivity and requires only a relatively small UV dose for crosslinking. An examples of reactive mesogen mixtures of the invention containing both electron-deficient and electron donor crosslinking groups is a 50:50 mixture of compounds 38 and 39. Mixtures of this type need not contain components having the same molecular core structure as is the case in this example.

Structure 38

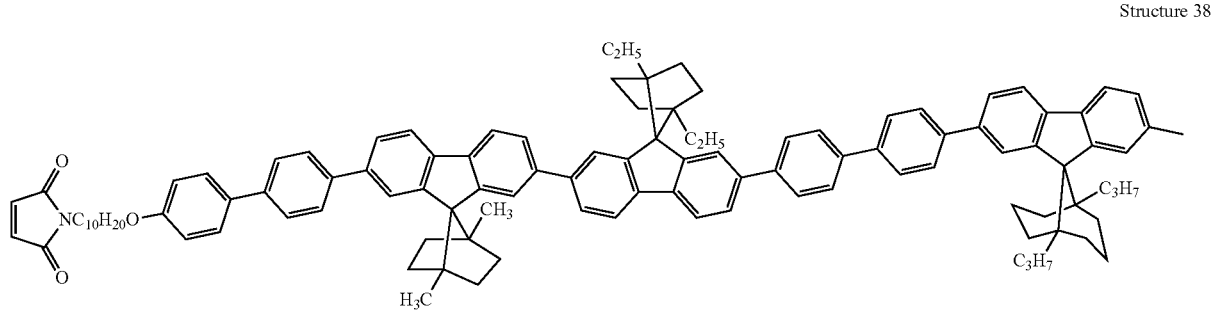

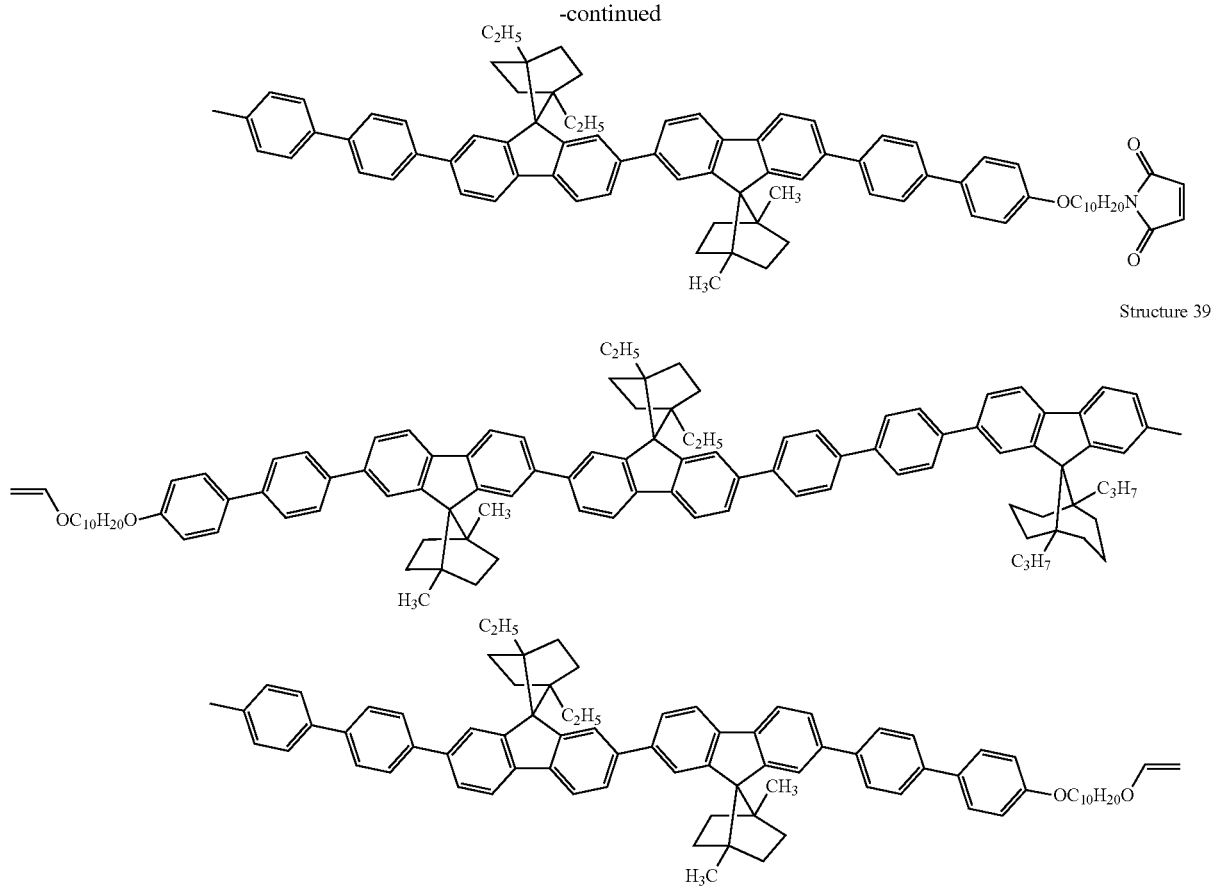

Structure 39

The exemplary OLED device 100 may be fabricated as follows. A substrate of indium-tin oxide coated glass (30 ohms/square) is patterned into a pixel or multipixel pattern a standard process of coating photoresist onto the substrate, patterning it with a UV light exposure through a photomask, developing the material, and then etching the ITO with 20% HCl/5% $HNO_3$. The photoresist is stripped from the ITO; the ITO is rinsed with D.I. water and then cleaned with an oxygen plasma. Hole injection layer 120 is formed by spin coating a 1.6% aqueous solution of Baytron P(AI 4083) polyethylene dioxythiophene polystyrene sulfonate (PEDT/PSS) available from N.C. Starck GmbH. onto the substrate glass over the patterned ITO. The substrate is then baked at 120° C. Next a 0.75% solution of compound 34 in chloroform is spin coated over the PEDT/PSS to form hole-transporting layer 130. The material is dried at 50° C. for 30 minutes and annealed at 90° C. for a minute. The material is then photocured using 351 nm. radiation from an argon ion laser at a fluence of 30 joules/$cm^2$. Then the light emitting layer 140 is formed by spin coating a chloroform solution consisting of 0.40% compound 37, 0.35% compound 35 and 0.05% compound 36 over layer 130. This layer dried and exposed to crosslinking UV exposure in the same way as was layer 130. Next electron transporting layer 150 is formed by spin coating a 0.75% chloroform solution of compound 37 over layer 140. This layer is then dried and photocured in the same way as were the previous layers. Finally an aluminium cathode is vacuum deposited over layer 150 yielding the device 100 represented in the drawing.

Figure 2:
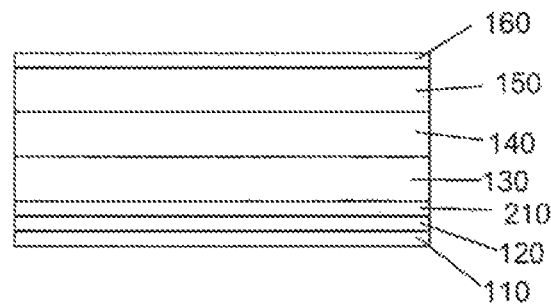
FIG. 2 illustrates a device in accordance with the present disclosure.

By using prior art techniques it is possible to insert a liquid crystal photoalignment material into device 100 as is shown in FIG. 2. In this new device 200 the hole transporting photoalignment layer 210 aligns the molecular long axes of the molecules in the spin coated liquid crystal layer from which hole injection layer 130 is formed by photocrosslinking. The alignment within 130 is such that the long axes of the liquid crystalline molecular core units within the polymer matrix forming the layer are parallel to each other and to the device substrate surface. The uniform alignment of the molecular cores in 130 aligns the long molecular axes of the liquid crystal molecules from which the light-emitting layer 140 is formed by acting as an alignment template. Similarly, the alignment of layer 140 acts as a template for the alignment of the liquid crystal molecules from which the electron-transporting layer 150 is formed. Thus, all three liquid crystal polymer layers, 130, 140, and 150, end up being uniformly aligned by the insertion of the alignment layer 210 forming the new device 200.

The formation of hole transporting, photoalignment layers like 210 is described in U.S. Pat. No. 7,118,787. These layers are formed by solvent casting, for instance from a 0.5% solution in cyclopentanone, a blend of a commercial photoalignment polymer, for instance a coumarin substituted polymethyl methacrylate like the material with structure 40, and a commercially available hole transporting material, for instance the triaryl substituted amine material (structure 41). The layer 210 is formed over the electron injection layer by solvent casting and the surface energy bias necessary to align the liquid crystal molecules is of the subsequent layers is induced by exposure to polarised UV light, for instance from the 300 nm spectral line of an argon ion laser.

Formula 40

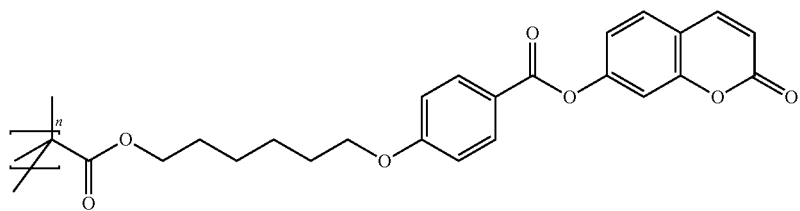

Formula 41

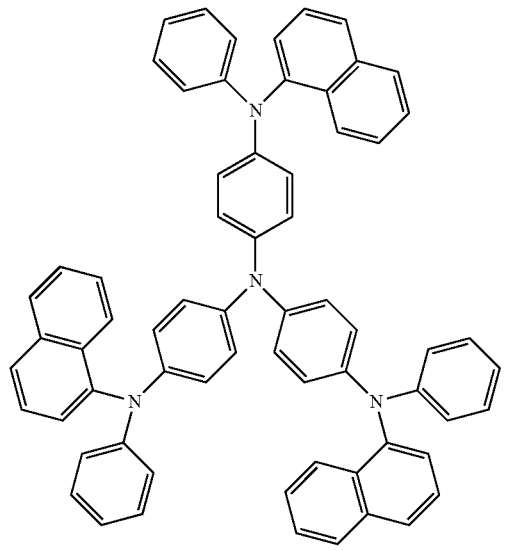

Devices like device 200 are useful because the light emitting, liquid crystalline polymer layers of the invention like 140 emit highly polarised light if they have their luminescent molecular cores uniformly aligned as they are in device 200. As a result, device 200 is an OLED that emits highly polarised light. OLEDs like 200 can find use as liquid crystal display backlights, in 3-dimensional displays, and in any other applications where the efficient emission of highly polarised light is advantageous. Aligned light emitting liquid crystalline layers of the types used in device 200 may also be advantageously used in other devices, for instance, photoluminescent polarisers.

Because the light emitting and charge transporting materials of the invention can be photopatterned like ordinary photoresists, they can easily and cost effectively be used to produce multicolour pixelated devices. For instance, a matrix array of green light emitting elements each having the structure of discrete device 100 may be fabricated on a glass substrate. Then a second array of the same number of blue light emitting elements may be fabricated with the same structure as 100, but by forming layer 140 by spin coating a chloroform solution consisting of 0.40% compound 37, 0.35% compound 42 and 0.05% compound 35 over layer 130 rather than using the formulation for layer 140 as in the example above. Finally an array of red light emitting elements equal in number to the green light emitting pixels may be fabricated with the same structure as 100, but by forming layer 140 by spin coating a chloroform solution consisting of 0.40% compound 37, 0.35% compound 35 and 0.05% compound 43 over layer 130. The arrays of the three different coloured light emitting elements may be arranged such that groups of one green emitting, one blue emitting, and one red light emitting element form a full-colour pixel group as is used in colour flat panel displays. It should be obvious that some device layers such as the hole injecting layer 120, the hole transporting, photoalignment layer 210, and the cathode 160 may be common to light emitting elements of all three colours.

Structure 42

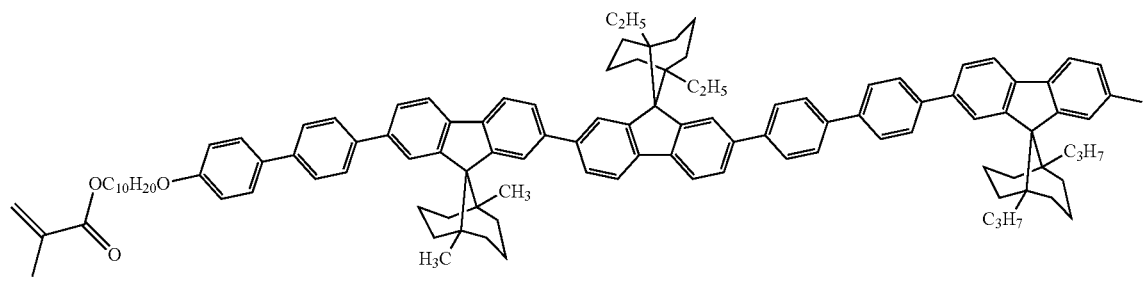

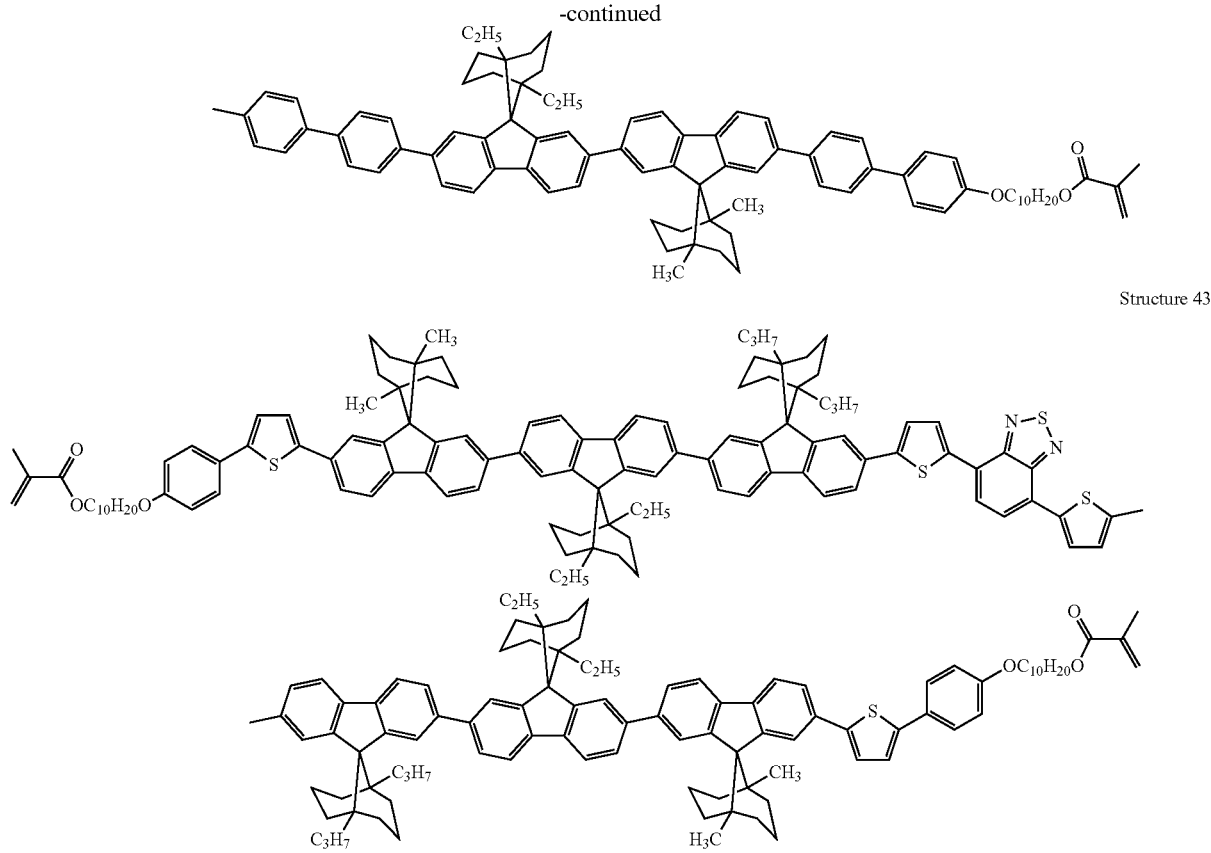

Structure 43

A further advantage of the materials described in this invention over more conventional OLED emitter and charge transporting materials is the ability for multiple layers to be cast then photocured into insoluble, immobile liquid crystalline polymer materials one over the other. Other polymeric OLED emitters and charge transporting materials remain solvent soluble after deposition onto device substrates with the result that subsequent material depositions from solvent would wash them away. This renders the fabrication of multilayer structures as in device 100 impossible. It should be obvious that devices with even more layers than device 100 can be easily fabricated by adding more deposition and curing steps.

The ability to cheaply and economically produce multilayer devices in which adjoining layers have different highest occupied or lowest unoccupied molecular orbital (HOMO and LUMO) energy levels as well as different charge carrier mobilities is of general utility in plastic electronics. For instance, the equivalent of p-n junctions may be formed using the materials and processes of this invention and these may find utility in diodes, transistors, and photovoltaic devices. The capability of the materials of the invention to be photolithographically patterned allows large arrays of plastic electronic devices of virtually any size and description to be fabricated.

The synthesis of the oxidation resistant materials of the invention proceeds through keto diester derivatives of alicyclic and bicyclic compounds such as VIII, XVIII, and XXVII in the following. These materials are produced by the alkylation of the enols of acetonedicarboxylic acid esters (VI and XVI). The keto compounds are then converted to the corresponding bromo compounds (X, XX, and XXIX). The bromides then undergo the Miyaura borylation reaction to yield the alkylboronic acid pinacol esters (XI, XXI, and XXX). These compounds are then coupled to the appropriate biphenyl derivative V. The Suzuki coupling reaction is not usually successful using boronates of this type because of the competing β-elimination reaction. However, because the boronates in this case have no β-substituted hydrogens, the competing reaction is not possible. The resulting intermediates are then ring-closed to the corresponding 9-spiro-substituted fluorenes diesters (XIV, XXIV, and XXXIII). The dieters may be converted to the desired alkyl substituted ring systems (for instance, XVII, XXVI, or XXXVI) by either reduction, or reaction with Grignard or alkyl lithium reagents followed by reduction.

The spiro-substituted fluorenes are the dihalogenated (Scheme 5) to ready them for incorporation into the reactive mesogen backbones. Schemes 6, 8, 7, and 9 portray the synthesis of reactive mesogen LVII using a series of Stille and Suzuki coupling reactions.

The synthesis of the oxidation resistant materials of the invention proceeds through keto diester derivatives of alicyclic and bicyclic compounds such as VIII, XVIII, and XXVII in the following. These materials are produced by the alkylation of the enols of acetonedicarboxylic acid esters (VI and XVI). The keto compounds are then converted to the corresponding bromo compounds (X, XX, and XXIX). The bromides then undergo the Miyaura borylation reaction to yield the alkylboronic acid pinacol esters (XI, XXI, and XXX). These compounds are then coupled to the appropriate biphenyl derivative V. The Suzuki coupling reaction is not usually successful using boronates of this type because of the competing β-elimination reaction. However, because the boronates in this case have no β-substituted hydrogens, the competing reaction is not possible. The resulting intermediates are then ring-closed to the corresponding 9-spiro-substituted fluorenes diesters (XIV, XXIV, and XXXIII). The diesters may be converted to the desired alkyl substituted ring systems (for instance, XVII, XXVI, or XXXVI) by either reduction, or reaction with Grignard or alkyl lithium reagents followed by reduction.

The spiro-substituted fluorenes are then dihalogenated (Scheme 5) to ready them for incorporation into the reactive mesogen backbones. Schemes 6, 8, 7, and 9 portray the synthesis of reactive mesogen LVII using a series of Stille and Suzuki coupling reactions.

Scheme 1: Synthesis of Biphenyl-2-yl Triflate

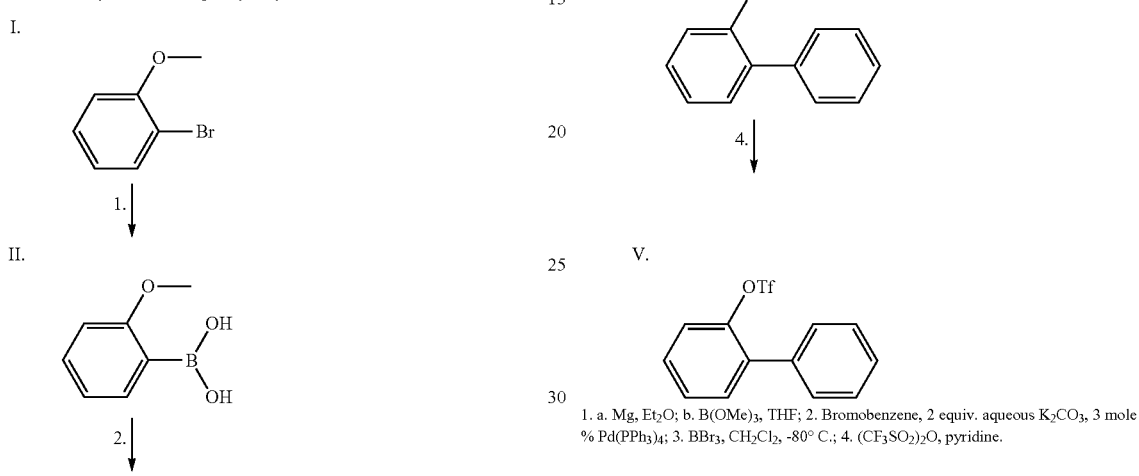

1. a. Mg, Et$_2$O; b. B(OMe)$_3$, THF; 2. Bromobenzene, 2 equiv. aqueous K$_2$CO$_3$, 3 mole % Pd(PPh$_3$)$_4$; 3. BBr$_3$, CH$_2$Cl$_2$, -80° C.; 4. (CF$_3$SO$_2$)$_2$O, pyridine.

Scheme 2: Synthesis of 1,4-dimethyl spiro[bicyclo[2,2,1]heptane-7,9'-fluorene]

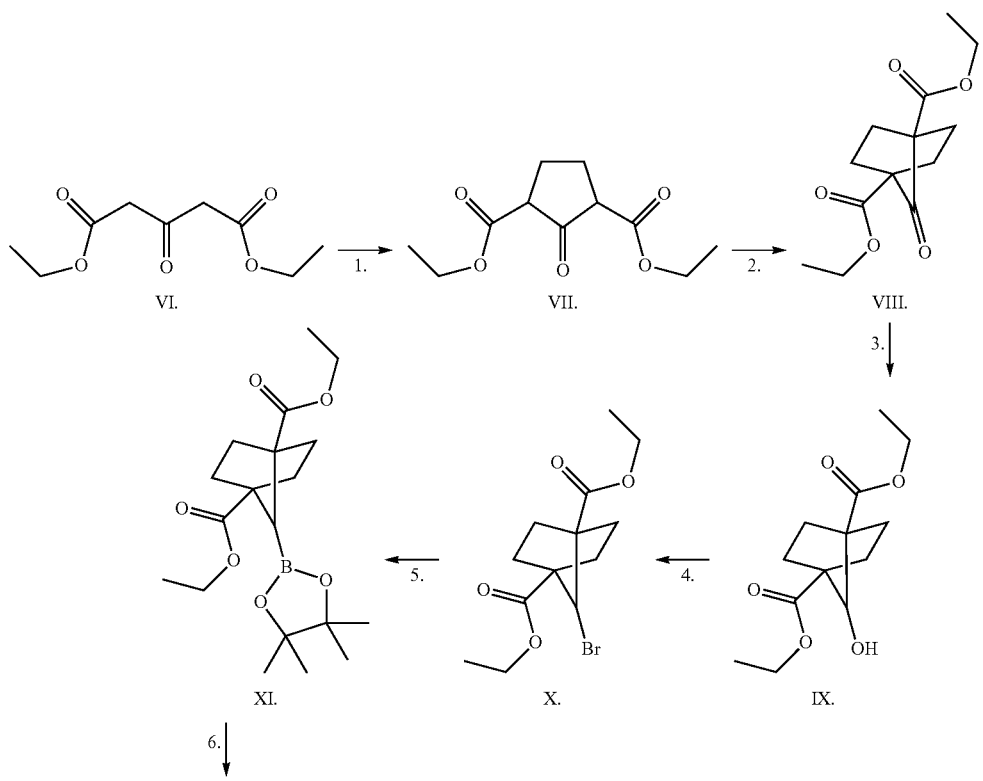

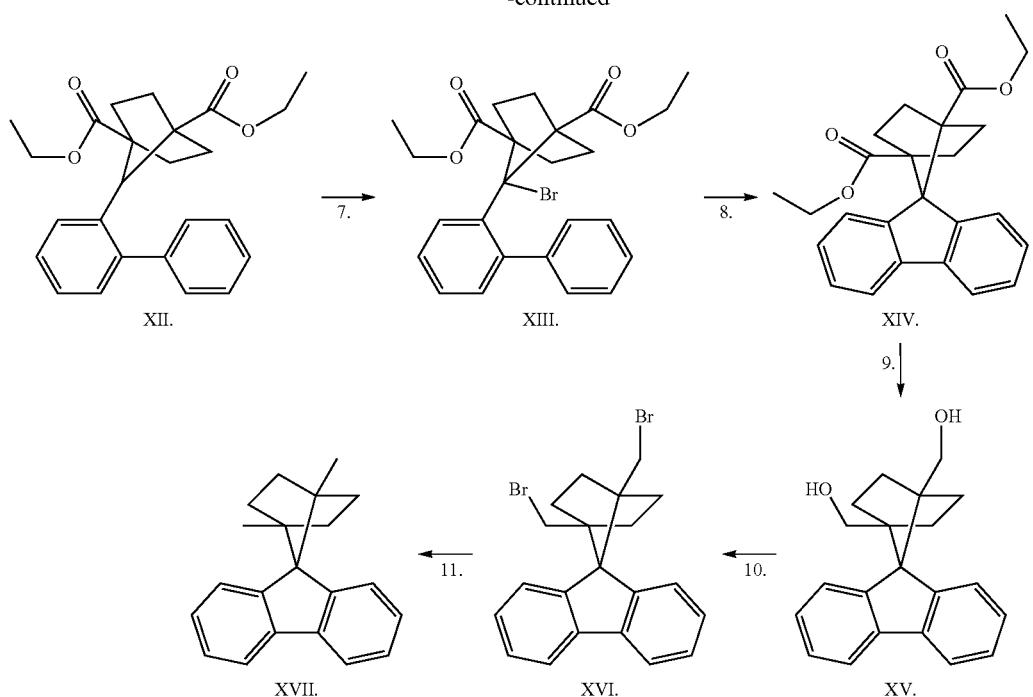

1. a. lithium diisopropylamide, THF; b. 1,2-dibromoethane, c. NaH, THF; 2. a. lithium diisopropylamide, THF; b. 1,2-dibromoethane, c. NaH, THF; 3. NaBH₄, CH₃OH; 4. Ph₃PBr₂, CH₃CN; 5. Bis(pinacolato)diboron, PdCl₂(dppf), aqueous KOAc, dioxane; 6. Compound V, Pd(PPh₃)₄, toluene, aqueous Na₂CO₃; 7. Br₂, CCl₄, dibenzoyl peroxide, UV light; 8. Boron triflouride etherate, THF; 9. LiEt₃BH, THF; 10. Ph₃PBr₂, CH₃CN; 11. LiEt₃BH, THF.

Scheme 3: Synthesis of 1,5-dipropyl spiro[bicyclo[3,3,1]nonane-9,9′-fluorene]

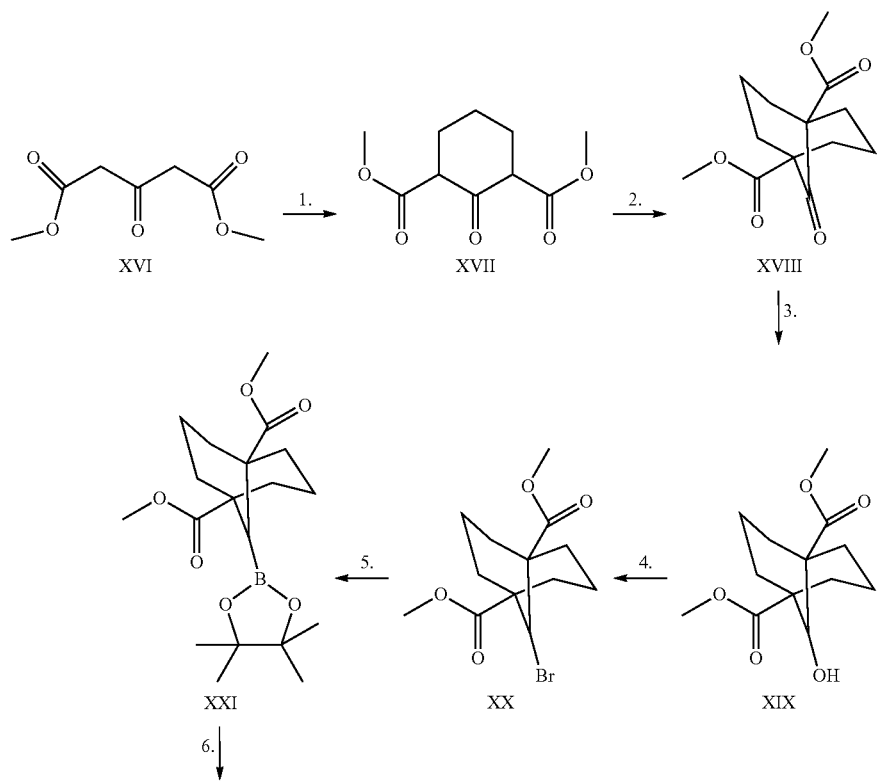

-continued

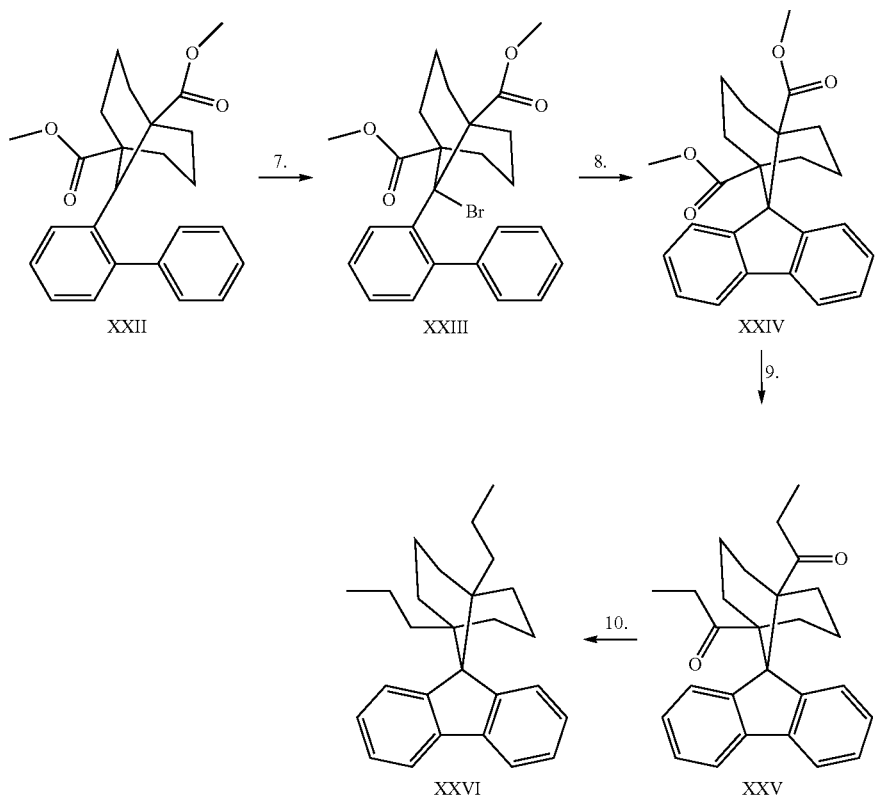

1. a. lithium diisopropylamide, THF; b. 1,3-dibromopropane, c. NaH, THF; 2. a. lithium diisopropylamide, THF; b. 1,3-dibromopropane, c. NaH, THF; 3. NaBH$_4$, CH$_3$OH; 4. Ph$_3$PBr$_2$, CH$_3$CN; 5. Bis(pinacolato)diboron, PdCl$_2$(dppf), aqueous KOAc, dioxane; 6. Compound V, Pd(PPh$_3$)$_4$, toluene, aqueous Na$_2$CO$_3$; 7. Br$_2$, CCl$_4$, dibenzoyl peroxide, UV light; 8. Boron triflouride etherate, THF; 9. a. C$_2$H$_5$MgBr, THF, b. dilute HCl; 10. a. H$_2$NNH$_2$•H$_2$O, N(C$_2$H$_5$OH)$_3$, reflux, b. KOH, reflux.

Scheme 4: Synthesis of 2,2,5,5-tetramethyl spiro[cyclopentane-1,9'-fluorene]

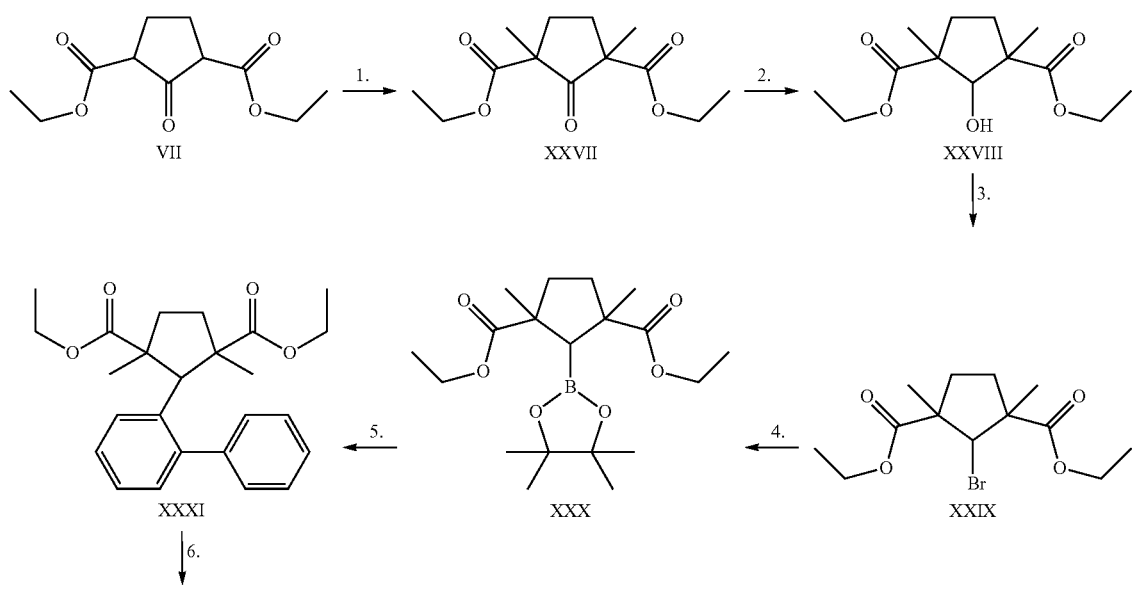

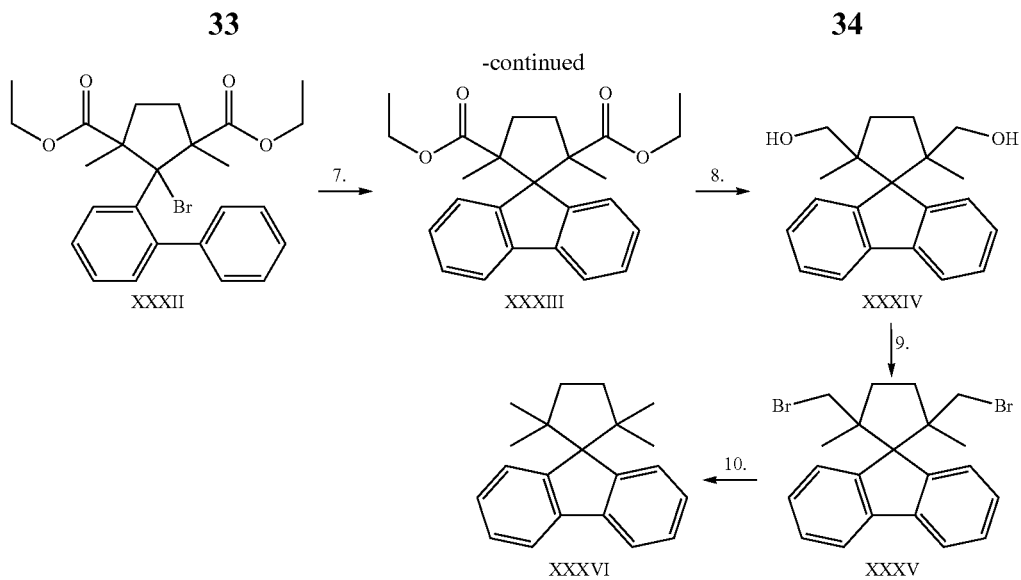

1. a. lithium diisopropylamide, THF; b. methyl iodide; 2. NaBH₄, CH₃OH; 3. Ph₃PBr₂, CH₃CN; 4. Bis(pinacolato)diboron, PdCl₂(dppf), aqueous KOAc, dioxane; 5. Compound V, Pd(PPh₃)₄, toluene, aqueous Na₂CO₃; 6. Br₂, CCl₄, dibenzoyl peroxide, UV light; 7. Boron triflouride etherate, THF; 8. LiEt₃BH, THF; 9. Ph₃PBr₂, CH₃CN; 10. LiEt₃BH, THF.

Scheme 5: Synthesis of 1,5-dimethyl spiro[bicyclo[3,3,1]nonane-9-9'-fluorene]

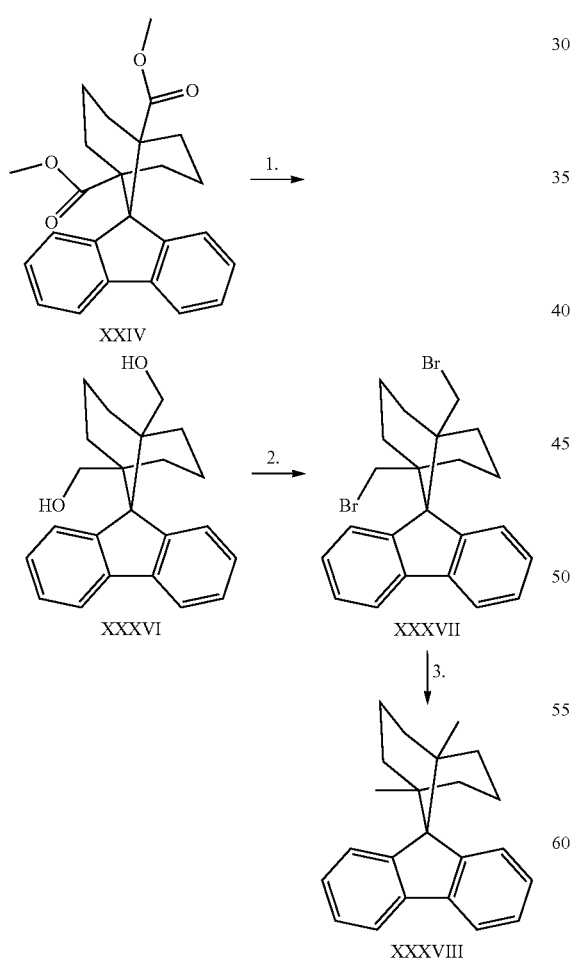

1. LiEt₃BH, THF; 2. Ph₃PBr₂, CH₃CN; 3. LiEt₃BH, THF.

Scheme 5: Synthesis of dihalofluorenes

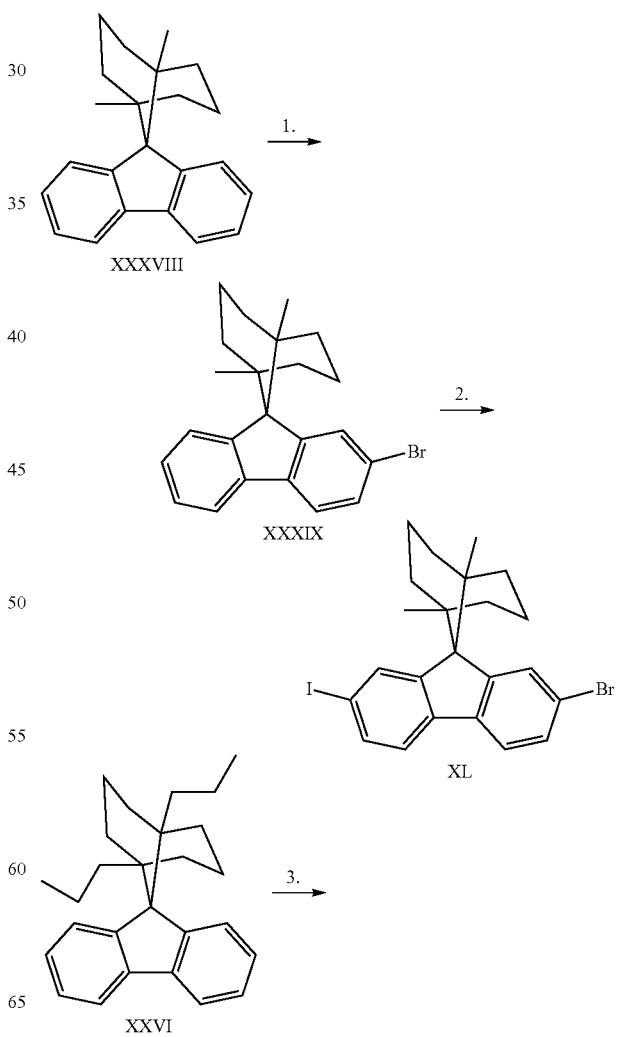

-continued
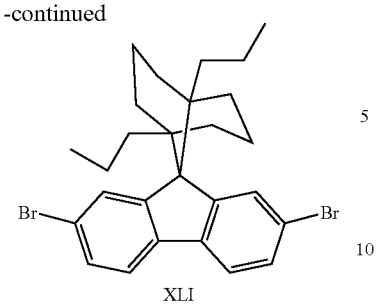
XLI
1. Br₂, CHCl₃; 2. I₂, HIO₄, CH₃COOH; 3. Br₂, CHCl₃
Scheme 6: Synthesis of Key Intermediate, 2',7'-bis(2,5-d[tri-n-butylstannyl]thieno[4,5-b]thienyl)-1,5-dipropyl spiro[bicyclo[3,3,1]nonane-9,9'-fluorene]
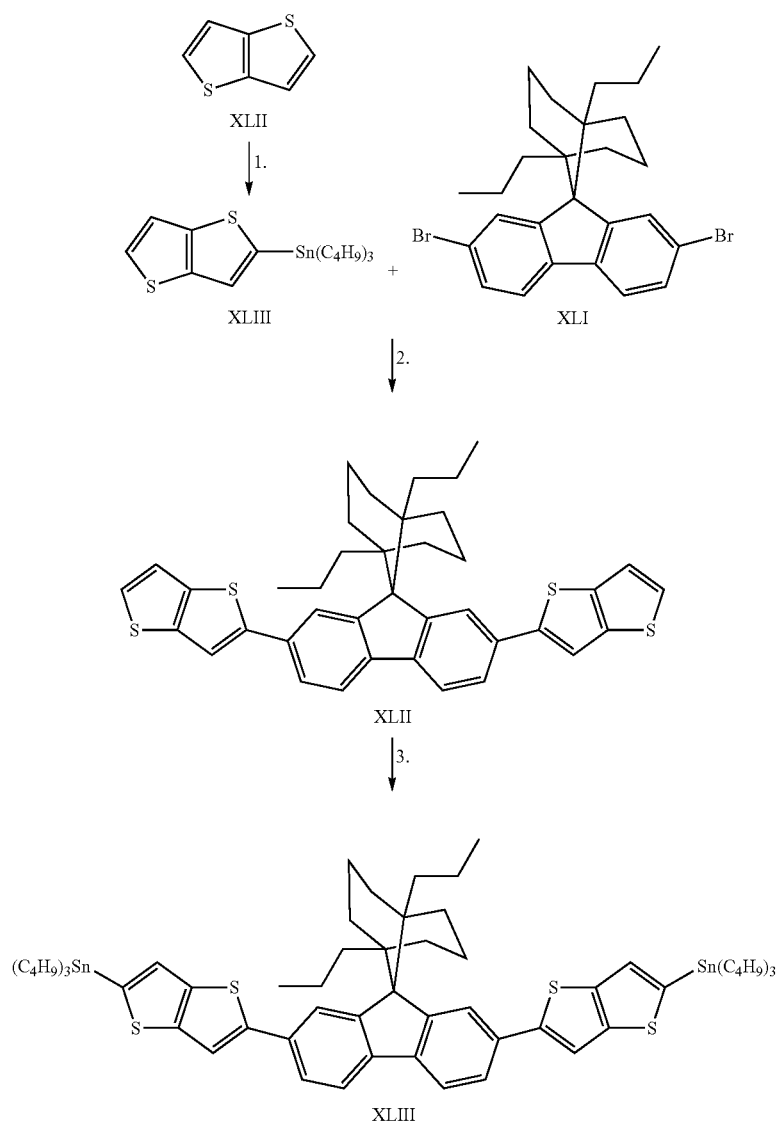
1. a. C₄H₉Li, THF (dry), -78° C., b. ClSn(C₄H₉)₃ (room temp.) 2. Pd(PPh₃)₄, DMF, 80° C.
3. a. C₄H₉Li, THF (dry), -78° C., b. ClSn(C₄H₉)₃ (room temp.)

Scheme 7: Synthesis of Spacer/Crosslinker
Scheme 8: Synthesis of Key Intermediate 7-([4-octyloxyphenyl]thien-2-yl) 2-(7-bromo{1,5-dimethyl spiro[bicyclo[3,3,1]nonane-9,9'-fluorene]}-2'yl) spiro[bicyclo[3,3,1]nonane-9,9'-fluorene]
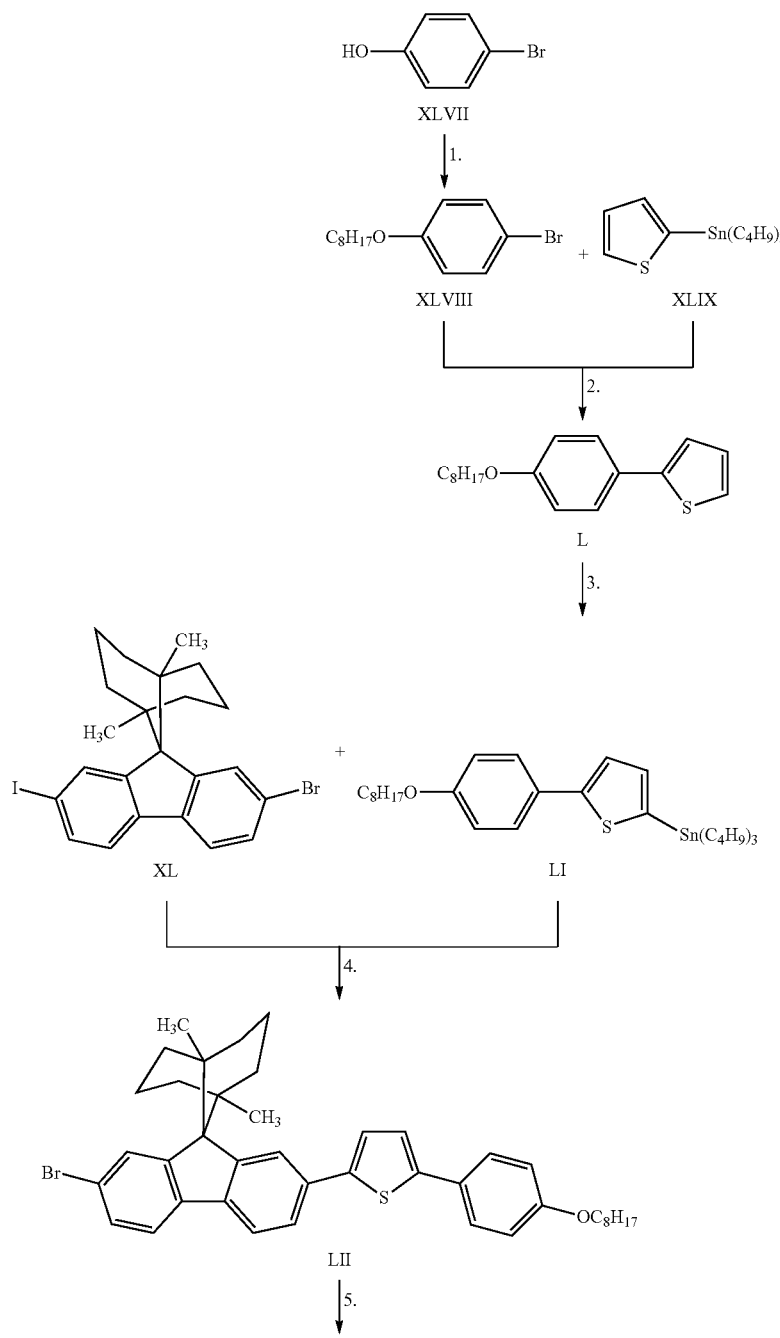

-continued
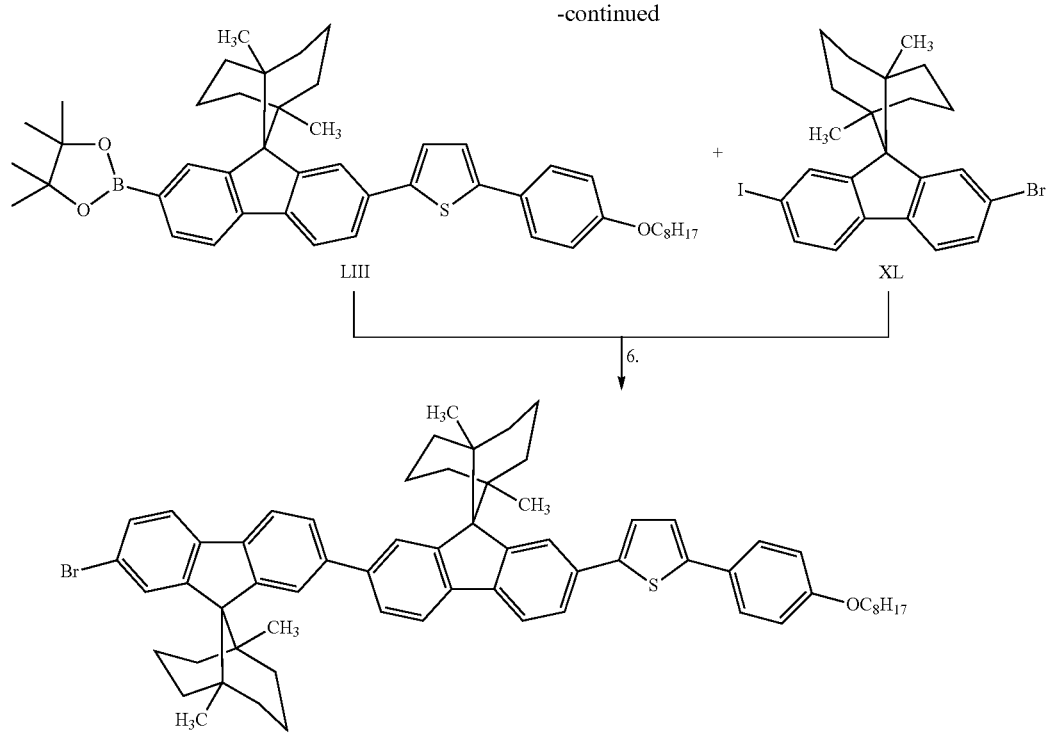
1. 1-bromooctane, $K_2CO_3$, butanone, reflux; 2. Pd(PPh$_3$)$_4$, DMF, 80° C.; 3. a. $C_4H_9Li$, THF (dry), -78° C., b. ClSn(C$_4$H$_9$)$_3$ (room temp.) 4. Pd(PPh$_3$)$_4$, DMF, 80° C.; 5 Bis(pinacolato)diboron, PdCl$_2$(dppf), aqueous KOAc, dioxane; 6. Compound XXXX, Pd(PPh$_3$)$_4$, toluene, aqueous Na$_2$CO$_3$;

Scheme 9: Synthesis of Electroluminescent Reactive Mesogen
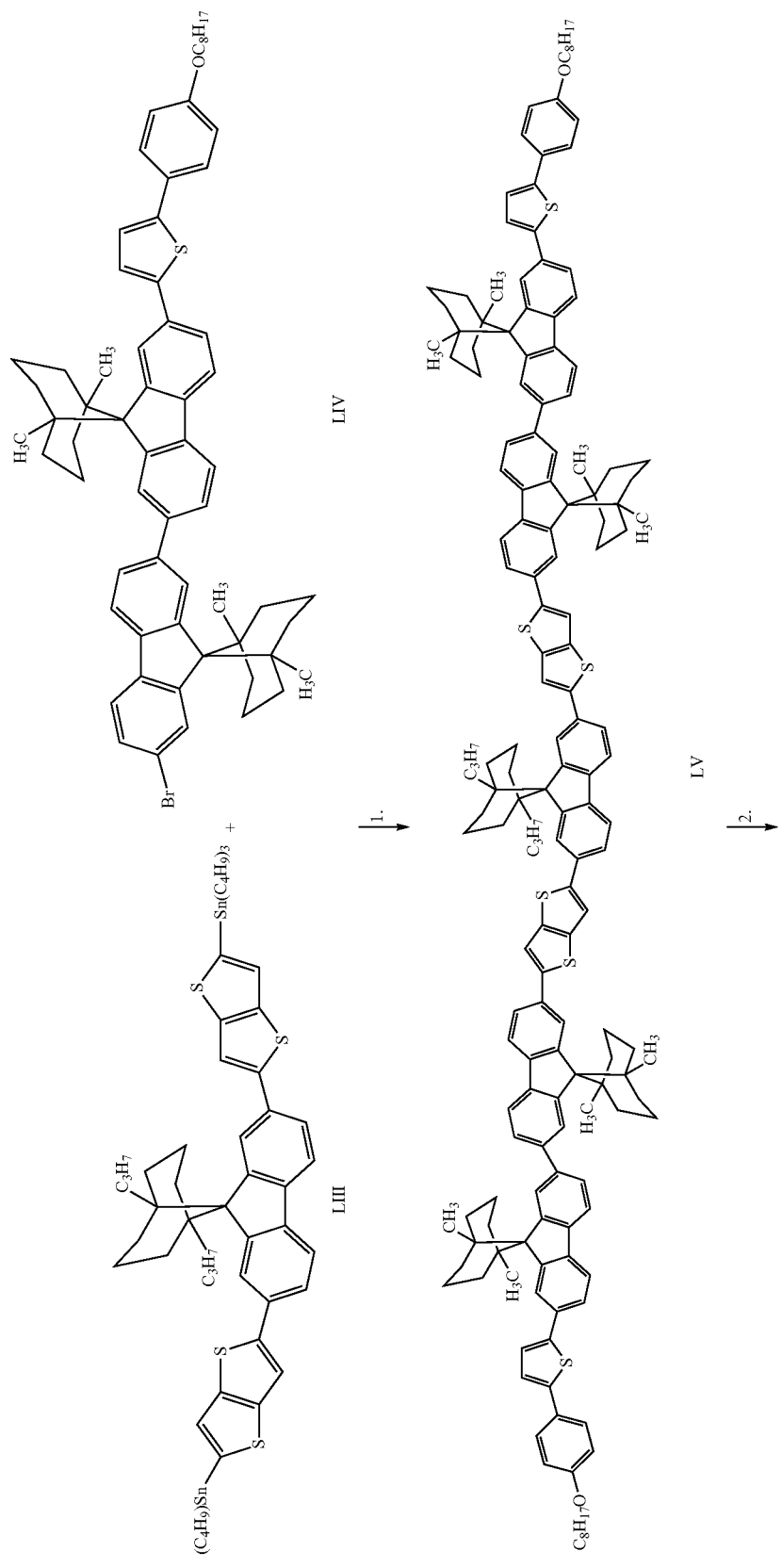

-continued
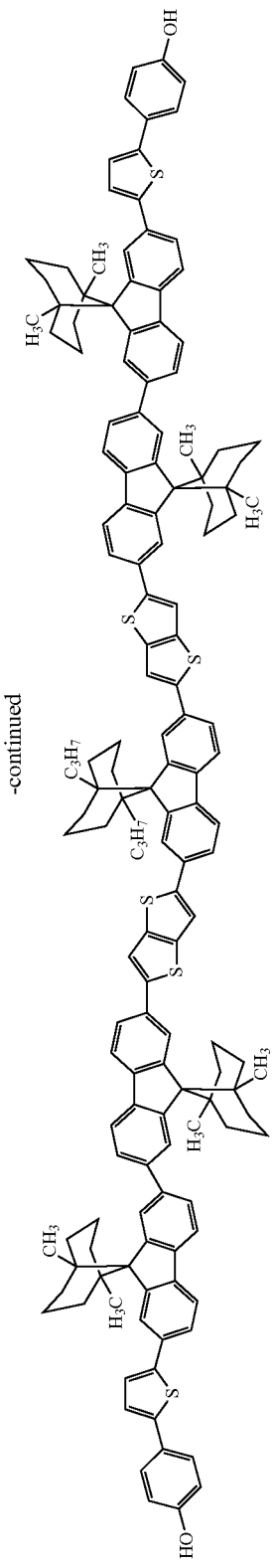
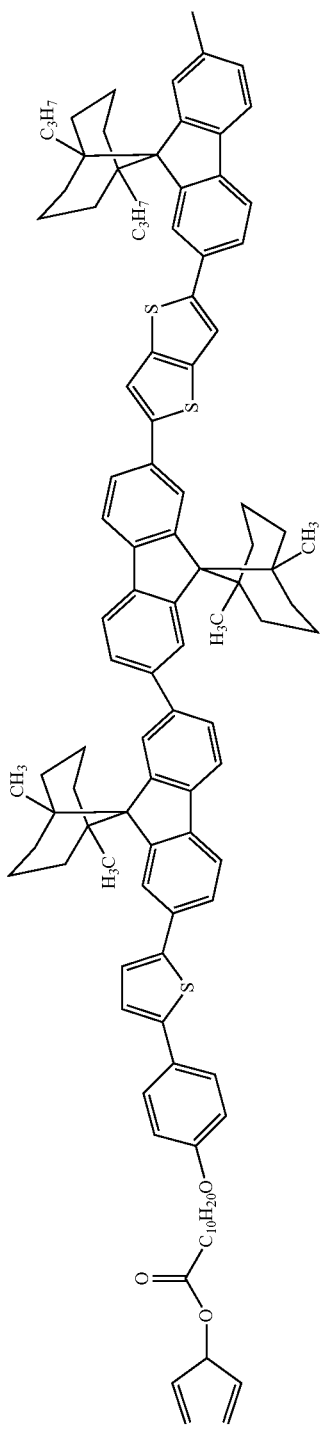
LVI
3.→
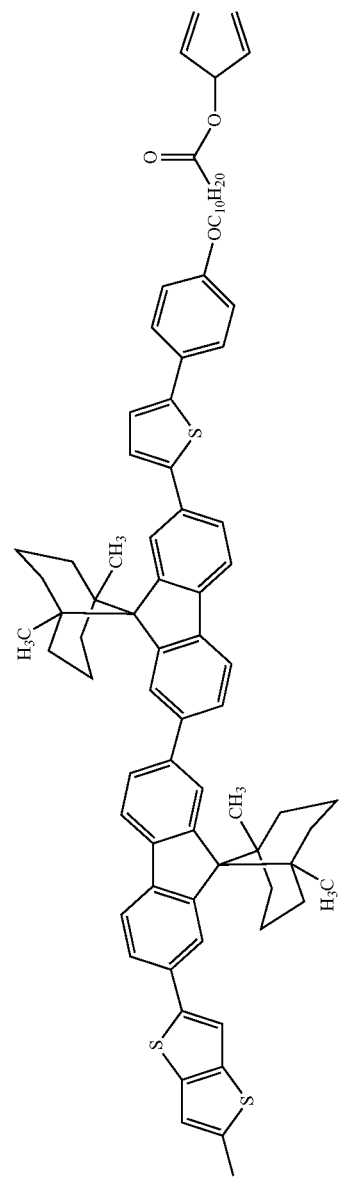
LVII
1. Pd(PPh₃)₄, DMF, 80° C.; 2. BBr₃, CH₂Cl₂, -80° C.; 3. Compound XLVI, K₂CO₃, acetonitrile Scheme 10: Synthesis of Electron Transporting Reactive Mesogen
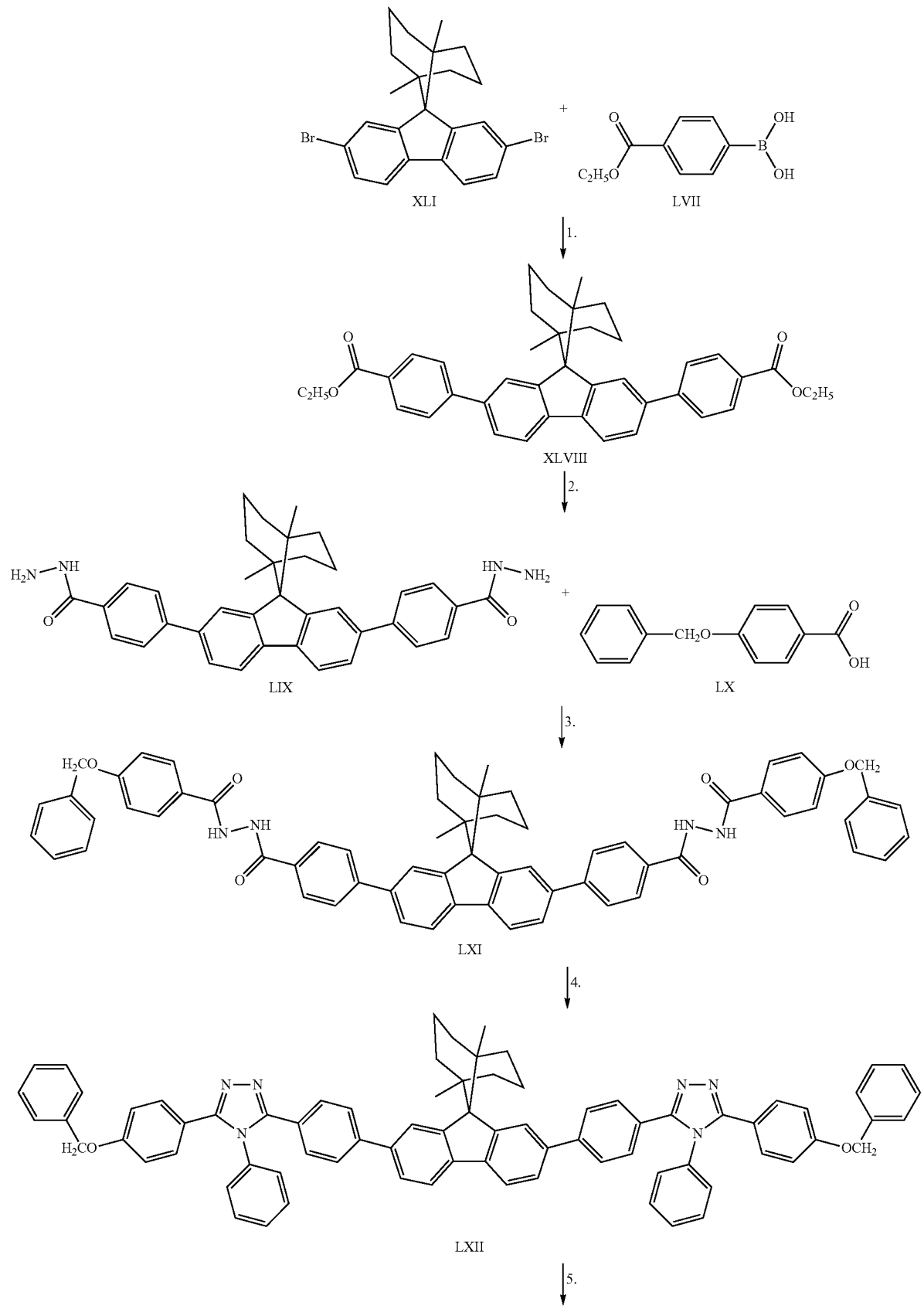

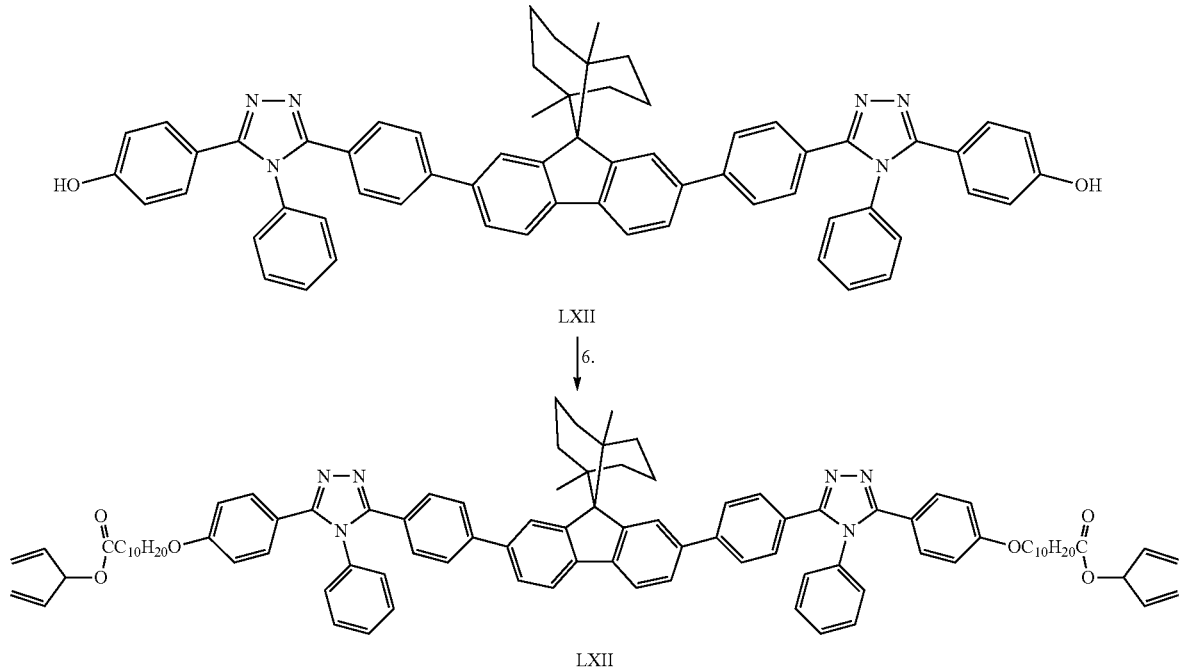

LXII

1. Pd(PPh$_3$)$_4$, toluene, aqueous Na$_2$CO$_3$; 2. H$_2$NNH$_2$, EtOH; 3. CH$_2$Cl$_2$, pyridine 4. Aniline, PCl$_3$, toluene; 5. H$_2$, Pd/C; 6. Compound XLVI, K$_2$CO$_3$, acetonitrile

The invention claimed is:

1. A compound of the general structure:

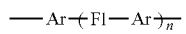

wherein A represents a linear, covalently bonded chain of the general formula:

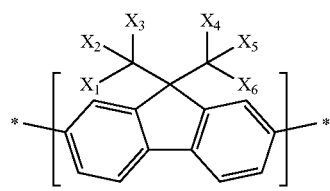

in which at least one Fl is a fluorene-2,7-diyldiradical of the structure:

wherein $X_1$, $X_2$, $X_5$, and $X_6$ are fluorines, and $X_3$ and $X_4$ are n-alkyl groups having the formula $C_mH_{2m+1}$ wherein m is from 1 to 12,

* indicates the point of attachment of Fl to the neighbouring groups, and wherein Ar in each occurrence is an aromatic diradical, a heteroaromatic diradical or a single bond, and wherein S represents a flexible spacer unit that is an alkyl group, optionally containing one or more heteroatoms, B represents a crosslinking group selected from the group consisting of a methacrylate, a 1,4-pentadien-3-yl, a maleimide, a maleate, a fumarate, and an alkenyl ether, and n is from 1 to 6.

2. The compound according to claim 1, in which B is a methacrylate group.

3. The compound according to claim 1, in which B is a 1,4-pentadien-3-yl group.

4. The compound according to claim 1, in which the Ar group is in each instance independently selected from a 1,4-phenylene, a biphenyl-4,4'-diyl, a terphen-4,4"-diyl, a naphthalene-1,4-diyl, a thiophene-2,5-diyl, a pyrimidine-2,5-diyl, a perylene-3,10-diyl, a pyrene-2,7-diyl, a 2,2'-dithiophen-5, 5'-diyl, an oxazole-2,5-diyl, a thieno[3,2-b]thiophene-2,5-diyl, a dithieno[3,2-b:2',3'-d]thiophene-2,6-diyl, an imidazo[4,5-d]imidazole-2,5-diyl diradical, and a single bond.

5. The compound according to claim 1, in which at least one Ar group is a 3,4,5-triaryl substituted 1,2,4-triazole.

6. The compound according to claim 1, wherein the compound exhibits a monotropic liquid crystalline phase.

7. The compound according to claim 1, wherein the compound exhibits a monotropic nematic phase.

8. The compound according to claim 1, wherein the compound exhibits a monotropic smectic phase.

9. The compound according to claim 1, wherein the compound is a phosphorescent light emitter.

10. The compound according to claim 1, in which B is selected from the group consisting of a maleimide, a maleate or a fumarate.

11. The compound according to claim 1, in which B is an alkenyl ether.

12. The compound according to claim 1, wherein n is from 1 to 3.

13. The compound according to claim 1, wherein n is from 3 to 6.

14. The compound according to claim 1, wherein the alkenyl ether is selected from the group consisting of a vinyl ether and a propenyl ether.

15. The compound according to claim 1, wherein S contains one or more heteroatoms.

16. The compound according to claim 1, in which at least one Ar group is a 3,4,5-triaryl substituted 1,2,4-triazole and a second Ar group is a 1,4-phenylene, a biphenyl-4,4'-diyl, or a terphen-4,4''-diyl.

17. The compound according to claim 1, in which at least one Ar group is a 3,4,5-triaryl substituted 1,2,4-triazole and a second Ar group is a thiophene-2,5-diyl, a 2,2'-dithiophen-5,5'-diyl, a thieno[3,2-b]thiophene-2,5-diyl, or a dithieno[3,2-b:2',3'-d]thiophene-2,6-diyl, 18. The compound according to claim 1, in which at least one Ar group is a 3,4,5-triaryl substituted 1,2,4-triazole and a second Ar group is a naphthalene-1,4-diyl, a pyrimidine-2,5-diyl, a perylene-3,10-diyl, a pyrene-2,7-diyl, an oxazole-2,5-diyl, or an imidazo[4,5-d]imidazole-2,5-diyl diradical.

* * * * *